US006829540B1

(12) United States Patent
Pidgeon et al.

(10) Patent No.: US 6,829,540 B1
(45) Date of Patent: Dec. 7, 2004

(54) DRUG DISCOVERY USING MULTIPLE MEMBRANE MIMETIC AFFINITIES

(75) Inventors: Charles Pidgeon, West Lafayette, IN (US); Hanlan Liu, Woodland Hills, CA (US); Kimberly Hauer, York, PA (US); Jianming Yin, Woodland Hills, CA (US); Song J. Cai, Keasbey, NJ (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 09/486,168

(22) PCT Filed: Aug. 21, 1998

(86) PCT No.: PCT/US98/17398

§ 371 (c)(1),
(2), (4) Date: Feb. 22, 2000

(87) PCT Pub. No.: WO99/10522

PCT Pub. Date: Mar. 4, 1999

Related U.S. Application Data

(60) Provisional application No. 60/056,833, filed on Aug. 22, 1997.

(51) Int. Cl.[7] ........................... G01N 33/48; G01N 1/00; G01N 15/00

(52) U.S. Cl. ............................. 702/22; 702/19; 422/50; 422/68.1; 530/413

(58) Field of Search ..................... 702/19, 22; 530/413; 422/68.1, 73, 50; 435/530

(56) References Cited

U.S. PATENT DOCUMENTS

| 5,025,388 A | 6/1991 | Cramer, III et al. |
| 5,307,287 A | * 4/1994 | Cramer et al. ................. 703/2 |

OTHER PUBLICATIONS

"Predicting Drug–Membrane Interactions by HPLC: Structural Requirements for Chromatographic Surfaces" by Hanlan Liu, Shaowei Ong. Louis Glunz: and Charles Pidgeon: Anal. Chem. (1995) vol. 67, 3550–3557.

"Calculation of Retention Times of Anthocyanins with Orthogonalized Topological Indices" by Dragan Amic and Dusanka Davidovic–Amic; J. Chem Inf. Comput. Sci. (1995) vol. 35, 136–139.

"Chemical Similarity Using Physiochemical Property Descriptors" by Simon K. Kearsley, Susan Sallamack, Eugene M. Fluder, Joseph D. Andose. Ralph T. Mosley, and Robert P. Sheridan (1996) vol. 36. 118–127.

"Structure–Activity Study of β–Adrenergic Agents Using the SIMCA Method of Pattern Recognition" by W.J. Dunn, II. Svante Wold and Y.C. Martin: J. Med. Chem. (1978) vol. 21, No. 9. 922–930.

(List continued on next page.)

*Primary Examiner*—Mary K. Zeman
*Assistant Examiner*—Lori A. Clow
(74) *Attorney, Agent, or Firm*—Barnes & Thornburg

(57) ABSTRACT

The measurement of multiple membrane affinities of test compounds, methods and compositions useful for acquiring data characteristic of such affinities, and a method and system for using such data alone or in combination with other molecular descriptors for the prediction of biological activity are described. The numerical values characteristic of biologically relevant interaction of test compounds with membrane mimetic surfaces are compared with corresponding values of one or more control compounds having a known biological activity. Probable biological activity of a test compound is identified with those control compounds whose multiple membrane interaction values most closely correlate to those of the test compound.

30 Claims, 2 Drawing Sheets

OTHER PUBLICATIONS

Gillet, Valerie J. et al., "Identification of Biological Activity Profiles Using Substructural Analysis and Genetic Algorithms", *J. Chem. Inf. Comput. Sci.*, vol. 38, 165–179 (1998).

Seelig, Anna et al., "A method to determine the ability of drugs to diffuse through the blood–brain barrier", *Proc. Natl. Acad. Sci. USA*, vol. 91, 68–72 (1994).

Sadowski, Jens et al., "A Scoring Scheme for Discriminating between Drugs and Nondrugs", *J. Med. Chem.* vol. 41, 3325–3329, (1998).

Ajay, W. Patrick Walters et al., "Can We Learn To Distinguish between "Drug–like" and "Nondrug–like" Molecules?", *J. Med. Chem.*, vol. 41, 3314–3324, (1998).

* cited by examiner

DRUG DISCOVERY USING MULTIPLE MEMBRANE MIMETIC AFFINITIES

CROSS-REFERENCES TO RELATED APPLICATIONS

This application is a U.S. national application of international application serial No. PCT/US98/17398 filed Aug. 21, 1998, which claims priority to U.S. provisional application Ser. No. 60/056,833 filed Aug. 22, 1997.

GOVERNMENT RIGHTS

Research relating to this invention was supported in part by the U.S. Government under Grant No. CTS9214794 awarded from the National Science Foundation. The U.S. Government may have certain rights in this invention.

FIELD OF THE INVENTION

This invention relates to prediction of biological properties. More particularly, the present invention is directed to the measurement of multiple membrane affinities of test compounds, methods and compositions useful for acquiring data characteristic of such affinities, and a method and system for using such data alone or in combination with other molecular descriptors for the prediction of biological activity.

BACKGROUND AND SUMMARY OF THE INVENTION

There has been much research and development effort directed to the definition of screening methods capable of identifying drug leads. The goal of such efforts is to define efficient methodologies for predicting biological activity in vivo by using empirically definable (or calculatable) descriptors to predict biological activity without the time investment and expense in costly animal studies. For many years most drug screening methods were based on conventional biological activity assays. More recently assays have been developed that predict cell membrane transport properties of test compounds. Generally drug leads are generated by comparing biological and physical properties of test compounds with known compounds having recognized biological activity in vivo. There is a significant body of literature directed to prediction of biological activities based on comparison of physical, chemical and biological descriptors and the use of pattern recognition analysis of such descriptors as part of drug screening protocols.

The present invention is directed to a method of screening test compounds for probable biological properties based principally on correlation of numerical values characteristic of their interaction with two or more membrane mimetic surfaces with corresponding values for control compounds of known biological activities/function. The method is grounded on the premise that compounds with similar sets of membrane binding properties will have similar pharmacological properties and/or biological activities. The membrane binding properties of test compounds can be calculated, or they can be determined empirically with use of, for example, liposomes, immobilized artificial membranes, such as those described in U.S. Pat. No. 4,931,498, the disclosure of which is incorporated herein by reference, Langmuir-Blodgett films, computer chips or similar devices with immobilized lipids, capillary zone electrophoresis columns coated with membrane lipids, and the like.

In one embodiment of this invention vector calculus is utilized to pattern match membrane interaction values of test compounds with control compounds to predict biological properties. The pattern matching protocol can be applied to data sets containing only values characteristic of multiple membrane interactions, or such data sets can include other biologically significant molecular descriptors such as molecular surface area, molecular weight, dipole moment, octanol-water partition coefficients, molecular volume, membrane diffusion coefficients, metabolism rates, cell efflux rates, etc.

In another embodiment, membrane binding data are obtained for test compounds and control compounds for use in accordance with this invention using immobilized artificial membrane chromatographic substrates in high pressure liquid chromatographic systems using aqueous mobile phases. Data relevant to the thermodynamics and kinetics of compound/membrane interaction is reflected in retention time and peak width, respectively. All data are preferably normalized relative to a standard compound or a set of compounds, for example, a set of compounds having a common biological activity or function.

This invention also provides novel carboxyl-functional, head group-protected phospholipids useful for preparing immobilized artificial membrane structures useful for acquiring membrane interaction data. They are prepared by novel high yielding transphosphitidylation of phosphatidylcholine derivatives using phospholipase D in the presence of protected alcohols.

DETAILED DESCRIPTION OF THE INVENTION

Figure 1:
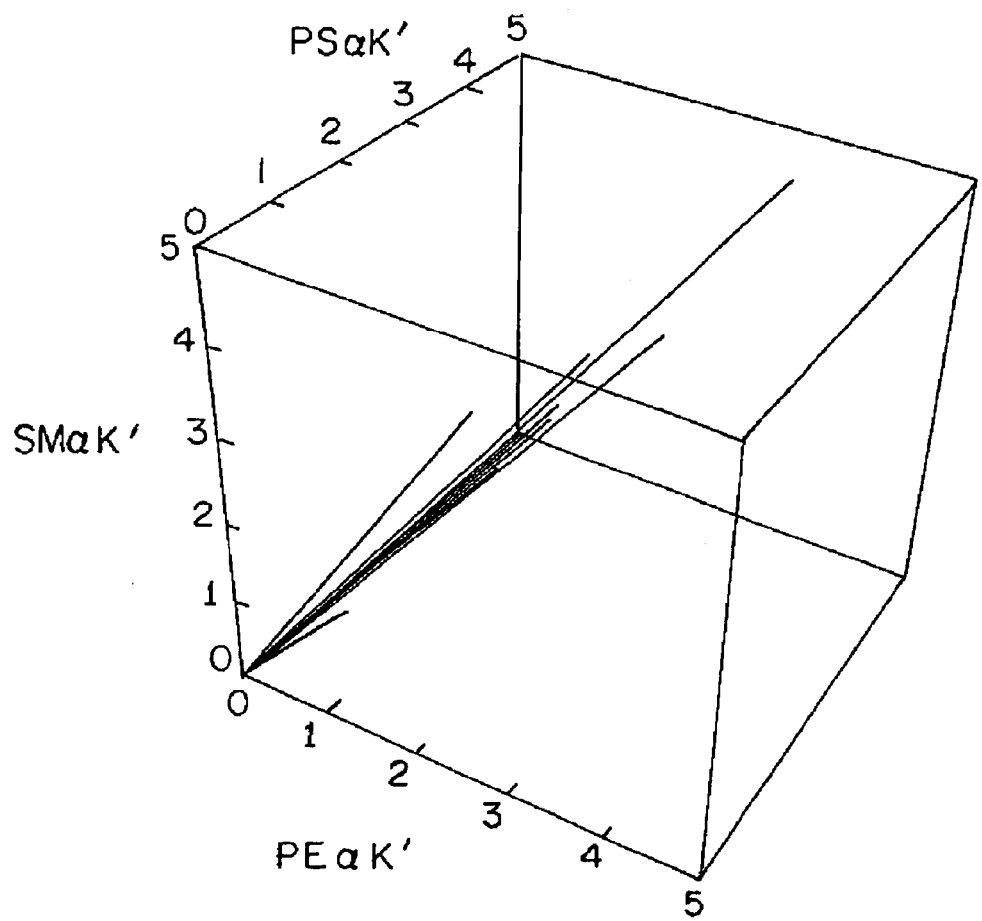
FIG. 1 is a 3-dimensional vector plot of membrane affinity data for compounds known to act at serotonin receptors.

In accordance with this invention in vitro membrane binding model was established to predict biological activity of compounds independent of both receptor binding assays and in vivo experiments. The membrane binding model was developed based on measurement of membrane binding constants of biologically active compounds on membrane mimetic surfaces. Collectively, the membrane binding data demonstrate that compounds within therapeutic classes exhibit similar binding profiles on amphiphilic/membrane mimetic surfaces and concomitantly similar tendencies to distribute into tissue lipid pools where activity is elicited.

Lipid heterogeneity in cell membranes functions to regulate the distribution and activity of many drugs. A drug compound with affinity for a particular lipid will accumulate in lipid pools enriched with that lipid. Examples include vinblastin and chlorpromazine which accumulate in the inner leaflet of plasma membranes because phosphatidyl serine (PS) and phosphatidyl inositol (PI) are enriched on the cytoplasmic side of cells. Drug-lipid interactions have been used to explain biological activity, the volume of distribution of drugs, drug binding to membrane receptors, and drug conformation in membranes. Boundary lipids near membrane receptors can play a key role in sequestering compounds and presenting membrane associated compounds to the receptor, or they can participate directly in regulating receptor function. Although such may not be true for all membrane receptors, it has been documented for several receptors. The results from the experimental work upon which this invention is based demonstrates that compounds with similar biological activity exhibit similar membrane binding properties.

Due to chemically precise ligand-receptor binding criteria, the drug discovery process traditionally focused on the structure of compounds as the dominant factor governing biological activity. However, it has now been observed that structurally diverse compounds within a given therapeutic class exhibit similar membrane binding properties indicates a cooperative role between the receptor and its adjacent membrane. Thus, the in vitro membrane binding model presented in accordance with this invention provides new insight regarding the criteria needed for a compound to elicit a given biological activity. Since both the receptor and its surrounding membranes contribute to a compound eliciting a particular biological activity, receptor binding assays used in conjunction with the present in vitro membrane binding model provides a synergistic approach to screening potential therapeutic compounds.

In accordance with one embodiment of the present invention, a method of screening test compounds for probable biological properties is provided. The method comprises the steps of identifying two or more membrane mimetic surfaces each having a unique amphiphilic composition. A set of control compounds is selected for comparison purposes. Each control compound has a known biological property, for example, a biological activity or interaction with a known receptor type.

The control compounds can have a common property, or they can be selected to represent widely variant biological properties. For each control compound there is defined an ordered set of numerical values characterizing a biologically relevant interaction (e.g., affinity) of that compound with each of the selected membrane mimetic surfaces. The ordered set of numerical values for each control compound or each set of control compounds (i.e., a "training set" as described below) can be represented by the expression $<C_1, C_2 \ldots C_n>$ wherein n is the number of membrane mimetic surfaces identified and used in the screening method. A similar ordered set of numerical values $<T_1, T_2 \ldots T_n>$ for each test compound characteristic of its biologically relevant interaction with each of the respective membrane mimetic surfaces is determined. The set of numerical values for the test compound is then compared with the sets of respective values for the control compounds, and the biological properties of those control compound having ordered sets of numerical values best matching the respective numerical values in the ordered set of values for the test compound is identified. The values $C_1, C_2 \ldots C_n$ and $T_1, T_2 \ldots T_n$ can be determined by computer calculations or empirically by any one or more of a wide variety of art-recognized techniques for evaluating membrane interactions.

In one embodiment of this invention the numerical values characteristic of membrane affinity are determined chromatographically using an aqueous mobile phase and a stationary phase comprising a membrane mimetic surface, for example, in a high performance liquid chromatographic system such as that described in U.S. Pat. No. 4,931,498, expressly incorporated herein by reference. The term "membrane mimetic surface" as used in describing and defining the present invention refers to any surface bearing immobilized amphiphilic molecules (i.e., those having both lipophilic and hydrophilic portions capable of exhibiting some selective affinity for or otherwise interacting with a solute (e.g., a test or control compound) in a fluid phase in contact with the surface. The term is intended to encompass a broad scope of commercially available stationary phases detailed for use chromatographic applications. Preferred membrane mimetic surfaces are those described in the above-incorporated U.S. Pat. No. 4,931,498.

Thus, in application of one embodiment of this invention membrane binding properties of a test compound of unknown biological activity are compared to the membrane binding properties of compounds having known in vivo biological activity to assess the probability that the test compound will exhibit one or more biological activities in vivo. The analysis is made by pattern matching membrane binding constants measured on immobilized artificial membrane columns in a high performance liquid chromatography system. Two or more immobilized artificial membrane chromatographic columns are used. Each test compound is injected and chromatographed on each column and the peak width and the peak time of the test compound is recorded and normalized to an internal or external standard. Thus experimentally measured selectivity values ($\alpha_{k'}=k'/k'$ standard) and normalized standard deviations ($\alpha_{sd}=\sigma/\sigma$ standard) were calculated for both the test compounds and compounds of known biological properties. Pattern matching using vector calculus, multivariate analysis or principal component analysis of the $\alpha k'$ and $\alpha_{sd}$ values of the test compound and the control compounds allows comparison of the membrane binding properties of the test compounds and each of the control compounds or, if the control compounds all have a common biological activity/property, average or mean membrane binding values of the set of control compounds for each membrane surface.

Important criteria for optimum implementation of the use of immobilized artificial membrane substrates for providing reliable values characteristic of membrane interaction include use of a stable membrane mimetic surface, preferably the same or a similar mobile phase composition and sample concentration, and use of a at least one common external standard. The external standard allows compensation for changes in measurements using the membrane surface from day-to-day and also lot-to-lot variation inherent in membrane mimetic preparations.

The external standard should be stable, it should be soluble in the aqueous mobile phase (typically organic phase modified), and it should have a reasonable retention time using said mobile phase and a high UV extinction coefficient. The external standard is typically injected in the HPLC/IAM system frequently to reflect temporal fluctuation in retention time. Normalization of the data eliminates variation among synthetic lots and from column deterioration and other factors that can cause temporal variability in retention times and peak width. One external standard which has been found to give good results when the mobile phase is 85% 0.01M PBS (pH 7.4)/15% acetyl nitrile is 4-methyl anisole. In one embodiment one or more sets of compounds, the members of each set having a common biological activity or function, are combined with one or more test compounds and loaded as a mixture onto a liquid chromatograph-mass spectrometer system to provide a direct comparison of binding properties of test and control compounds in that chromatographic system.

Membrane binding constants (k' values) are calculated in accordance with the formula $k'=(t_r-t_0)/t_0$ wherein $t_r$ is the retention time and $t_0$ is the dead time obtained from each injection; however, $t_0$ in the denominator was obtained by averaging the experimentally determined $t_0$ from all injections for each day the data are collected.

The use of chromatography on immobilized artificial membranes provides data characteristic of both equilibrium binding to the respective membrane mimetic surface (k' values) and the kinetics of mass transfer between the immobilized artificial membrane surface and the mobile phase (i.e. $\delta$ values). Similar to all chromatography columns, columns utilizing immobilized artificial membranes exhibit column-to-column and lot-to-lot variation. This unavoidable variation in the experimentally determined k' and δ values for each test compound and each control compound is eliminated, for pattern matching purposes, by normalizing k' and δ values to an internal or external standard compound chromatographed on each immobilized artificial membrane column. Thus k' and δ values for the test compounds are each divided by the respective k' and δ values of the standard to calculate $\alpha_{k'}$ and $\alpha_{sd}$, the selectivity values and normalized standard deviations, respectively. For k' values, α denotes the selectivity of the immobilized artificial membrane chromatographic surface for molecular recognition of the analyte; α is a thermodynamic property and corresponds to a ratio of membrane partition coefficients.

The values $T_1, T_2 \ldots, T_n$ ($\alpha_{k'}$ or $\alpha_{sd}$) for each test compound and the corresponding values $C_1, C_2 \ldots, C_n$ for each control compound can be conveniently stored in any database management system for subsequent retrieval and analysis. The comparison of the set of numerical values for each test compound with the sets of respective values or the control compounds can be carried out using any of a wide variety of mathematical analytical techniques.

In one embodiment of this invention the comparison is accomplished by multidimensional vector analysis of the data wherein the ordered set of numerical values for each test compound is compared to those corresponding values for each control compound, or, where the control compounds are all selected to have a common biological activity or biological function, an average or mean values for the selected set of control compounds. Thus, in one embodiment the control compounds best matching the values for the test compounds are those for which the angle Θ in the formula cosine $\Theta = (T_1C_1 + T_2C_2 + \ldots T_nC_n)/(T_1^2 + T_2^2 + \ldots T_n^2)^{1/2} (C_1^2 + C_2^2 \ldots C_n^2)^{1/2}$ is less than about 20°. The best match of membrane binding patterns between the test compound and the control compounds is that where the angle Θ in the above formula is a minimum. Where the number of membrane surfaces used in the method is two or three, each ordered set of numerical values for the test compound and the values for each respective control compound can be displayed graphically as a vector in a 2- or 3-dimensional coordinate system, respectively, to facilitate comparison of the numerical values of the test compound with those of the control compounds.

In one embodiment the test compound data are displayed as a uniquely discernible vector quantity, i.e., in a color different than the control compounds. Where the control compounds comprise a set of compounds having a predefined biological property, the numerical values for each member of said set of control compounds can be displayed as vector quantities uniquely discernible as a member of said set of control compounds and visibly distinguishable from the test compound. Alternatively, the data for the control compounds in a set of control compounds having a predefined biological property can be mathematically manipulated to define a mean or average membrane interaction value for each membrane species. The mean or average vector quantities calculated for the set of control compounds can be used in the above-described pattern matching analysis or they can be displayed graphically as uniquely discernible vector quantities with those of one or more test compounds.

Thus, in one embodiment of this invention the membrane binding properties of six hallucinogens were measured on immobilized artificial membranes (IAMs) prepared from phosphatidylcholine (IAM.PC), phosphatidylserine (IAM.PS), phosphatidylethanolamine (IAM.PE), and sphingomyelin (IAM.SM). Mean vectors were calculated for several therapeutic classes of compounds. The calculated mean vector (i.e., the average vector representing a group of compounds with similar biological activity) is shown in Table 1 for hallucinogenic compounds.

TABLE 1

Membrane binding properties of hallucinogens constitute a training set for analysis

| Compound | IAM.PC | IAM.PE | IAM.PS | IAM.SM |
|---|---|---|---|---|
| n-acetylmescaline | 0.706 | 1.323 | 0.736 | 1.051 |
| psilocin | 4.656 | 4.818 | 4.941 | 7.532 |
| (R)-2,5-dimethoxy-4-iodoamphetamine mescaline | 55.53 | 29.76 | 260.200 | 53.41 |
| 2,5-dimethoxy-4-bromoamphetamine | 15.260 | 20.950 | 143.400 | 20.970 |
| mescaline | 1.476 | 2.134 | 12.280 | 2.074 |
| p-iodoamphetamine | 24.880 | 33.660 | 258.100 | 32.410 |
| mean membrane binding properties (Mean vector) | 17.085 | 5.441 | 113.276 | 19.574 |

As shown in the last row of Table 1, the average vector representing the membrane binding properties of hallucinogenic compounds is {17.08 5.441 113.276 19.574} which corresponds to the membrane binding properties on {IAM.PC, IAM.PE, IAM.PS, IAM.SM}. The average vector of several other training (control) sets were calculated as shown for hallucinogens in Table 2. The goal is to compare the membrane binding constants of an unknown compound to the average vectors representing each class. As shown in Table 2, when the angle between an unknown compound (i.e., 3,4-methylendioxyamphetamine (MDA) in this example) was calculated relative to the average vector for each therapeutic class of compounds, the closest match was hallucinogens and the closest receptor match was serotonin.

TABLE 2

Comparison of MDA to the mean membrane binding properties of compounds within different therapeutic classes

| Activity | Angle |
|---|---|
| hallucinogens | 2.56 |
| antihypertensive | 2.770 |
| anorexic | 7.29 |
| stimulants | 15.27 |
| serotonin* | 23.26 |
| antidepressant | 27.77 |
| antiparkinson | 44.20 |
| anxiolytics | 48.16 |
| dopamine* | 49.33 |
| antipsychotic | 49.90 |
| γ-amino butyric acid* | 57.87 |
| opioid | 60.46 |
| sedative-hypnotics | 61.89 |
| anticonvulsant | 63.13 |

*receptor class.

These matches indicate that the test compound may have biological properties similar to hallucinogenic compounds and may act at serotonin receptors, which is indeed the case of MDA.

In one embodiment of this invention membrane binding constants are measured by injecting the drugs into high performance liquid chromatographs (HPLC) using immobilized artificial membrane (IAM) columns using the following IAM stationary phases:

$^{ester}$IAM.PC$^{C10/C3}$, $^{ester}$IAM.PE$^{C10/C3}$, $^{ester}$IAM.PS$^{C10/C3}$, and $^{ester}$IAM.SM$^{C10/C3}$ The peak position of the drug in the chromatogram is a measure of the affinity of the compound for the immobilized membrane surface. The retention time (peak time) was used to calculate the capacity factor, k', of the compound for the IAM surface. Capacity factors are proportional to equilibrium membrane binding constants K according to $$k' = \emptyset K$$

where $\emptyset$ is the phase ratio of the column. Effectively, the set of average k' values for a group of compounds with similar biological function constitute a membrane affinity fingerprint ($MAF^\mu$) of the biological function. Thus $MAF^\mu$ denotes a mean vector whereby the vector components are average membrane binding constants for a group of compounds (a training set) with similar biological activity or functionality, e.g., oral absorption.

Establishing Training Sets

The term "training set," as used to describe and claim this invention, is a set of compounds of common biological properties used to define/calculate an $MAF^\mu$ value for that biological property. Normally distributed membrane/membrane mimetic binding affinities in N-dimensional space occur when bivariate log plots of $\alpha k'$ (i.e. PC vs PE, PC vs PS, etc.) have an ellipsoidal shape. The ellipse shape indicates that the affinity data for a given set of compounds having a known clinical efficacy or function are normally distributed in 2 dimensional space. In the case when a compound falls outside of the 0.95 quartile (3 standard deviations from the mean), it is considered to be an outlier. Deletion of outliers increases the ellipticity of the bivariate data, thus improving the multivariate normality. For this reason, the general procedure used to establish a training set of compounds is to continuously (1) remove outliers, and (2) redraw the ellipse plot until all compounds fall within the 0.95 quartile. Ellipse plots were thus used to remove outliers and confirm that the membrane binding data were normally distributed in N-dimensional space. Ellipse plots for all possible combinations of membrane binding constants were used to define each training set: PC vs PE, PC vs PS, PC vs SM, PC vs PS, PE vs SM, and PS vs SM.

Accordingly, there is provided as another embodiment of this invention a composition comprising a mixture of compounds which have a common biological activity or function or clinical efficacy. Typically the compounds in the training set composition are in a predetermined molar ratio. In one embodiment the control compounds in the training set composition are in a substantially equimolar ratio, optionally in combination with one or more external standards. Preferably the compounds in this training set selected so that the ellipse plot of the membrane mimetic binding data for the compounds in the training set composition are such that all compounds fall within the 0.95 quartile. The training set typically includes at least two, preferably at least three, most preferably 5 or more control compounds. The training set composition can be combined with test compounds (and optionally training set compositions for other biological properties) to prepare mixture for LC/MS analysis of membrane/membrane mimetic binding properties. The training set compositions in accordance with this invention provide ideal internal controls for direct comparison of test compound affinities with those exhibited by the compound members of the training set in LC/MS analytical protocols.

Determining Mean Vectors

The mean membrane binding affinities for each training set are calculated by averaging the PC, PE, PS, and SM as illustrated in Table 3 for selected hallucinogen compounds: Multivariate Analysis of Variance (MANOVA) confirmed that greater than 90% of the mean membrane binding affinities of all therapeutic classes and mechanism of actions were different at the 0.05 confidence level. In other words, the mean vector for each training set developed for use in accordance with this invention was unique compared to all other training sets.

TABLE 3

Mean Vector or Membrane Affinity Fingerprint ($MAF^\mu$) for Hallucinogens.

| Compound | IAM.PC | IAM.PE | IAM.PS | IAM.SM |
|---|---|---|---|---|
| mescaline | −0.477 | 0.670 | 2.43 | −0.715 |
| psilocin | 0.900 | 1.79 | 2.80 | 0.502 |
| MDA | 0.298 | 1.32 | 3.28 | −0.0647 |
| DOB | 2.07 | 3.22 | 4.68 | 1.62 |
| DOI | 2.61 | 3.73 | 6.13 | 2.14 |
| Mean ($MAF^\mu$) | 1.08 | 2.15 | 3.87 | 0.696 |

The data in the above table is Ln weighted.

Predicting the Activity or Unknown Compounds $D^2$ and Q Values

In addition to the vector analysis method described above for calculation of angle $\Theta$ values, $D^2$ and Q values can also be used for classifying/comparing compounds by vector analysis of binding data (and other quantitative physicochemical properties). Membrane binding data for an unknown compound is an observation vector y, and the mean membrane binding data for the $i^{th}$ training set of compounds is denoted as the vector $y_i$. The classification of an unknown compound involves calculating the mean squared distance, $D^2$, between y and $y_i$.

$$D^2_i = (y-y_i)'S_i^{-1}(y-y_i)$$

where $S_i$ is the covariance matrix of the $i^{th}$ group of compounds. The unknown compound is assigned to the therapeutic class or receptor type with the smallest $D^2_i$ value.

An alternate method for classifying compounds is by use of Q values.

$$Q_i(y) = -\tfrac{1}{2} \ln|S_i| - \tfrac{1}{2}(y-y_i)'S_i^{-1}(y-y_i)$$

where $|S_i|$ is the determinant of the covariance matrix of the $i^{th}$ group. When Q values are used to classify compounds, the unknown compound is assigned to the therapeutic class with the highest Q value.

Both $D^2$ and Q were used to classify the activity of each compound comprising all of the training sets. A compound was considered to classic correctly when its known therapeutic class or mechanism of action was within the top two hits based on $D^2$ and Q. Table 4 shows the $D^2$ and Q values for the classification of MDA (a hallucinogen).

TABLE 4

$D^2$ and Q values for MDA compared to all therapeutic classes.

| Activity | $D^2$ | Q |
|---|---|---|
| hallucinogen | 3.20 | 5.27 |
| antiparkinson | 1.77 | −2.24 |
| anorexic | 9.14 | −2.38 |
| antihypertensive | 4.09 | −3.91 |
| analgesic | 10.6 | −5.34 |

TABLE 4-continued $D^2$ and Q values for MDA compared to all therapeutic classes.

| Activity | $D^2$ | Q |
|---|---|---|
| diuretic | 12.9 | −7.06 |
| antineoplastic | 0.991 | −9.06 |
| antidepressant | 24.6 | −10.7 |
| antipsychotic | 25.5 | −11.5 |
| nucleoside | 6.38 | −12.3 |
| antiviral | 31.7 | −13.5 |
| anticonvulsant | 52.0 | −24.0 |
| sedative hypnotic | 104 | −49.3 |

Order of Elution

The relative order of elution is a measure of the relative affinity of each compound for each membrane mimetic surface. Unfortunately, theta, $D^2$, and Q values for a compound of unknown activity do not necessarily reflect elution order. Thus a low theta and $D^2$ or large Q may occur even though a compound does not have the same relative order of elution exemplified by the mean vector of the most comparable training set. Consequently, in vivo activity can be predicted using not only theta, $D^2$, and Q values, but also the LC elution order of the unknown compound on the respective solid phase substrates vs that of the mean vector for a known training set.

Standard Deviations

Another parameter to consider when predicting the in vivo activity of a compound is the peak width associated with each membrane mimetic surface. Peaks widths evaluate the on-off kinetics of drug membrane interactions. For example, the unknown compound BDFA was evaluated for hallucinogenic activity. Its theta value relative to the hallucinogen $MAF^{\mu}$ was 3.6 and its order of elution matched that of the hallucinogen $MAF^{\mu}$. However, the peak widths of BDFA on SM and PS are much larger than the corresponding peak width of $MAF^{\mu}$. In vivo studies have shown that BDFA is inactive. Both the theta value and order of elution indicate that BDFA would be active in vivo. Only the difference in the peak widths provided evidence that BDFA would be inactive in vivo.

In accordance with another embodiment of the present invention there is provided a system for screening test compounds for probable biological properties. The system comprises two or more membrane mimetic surfaces, each having a unique amphiphilic composition. The system includes means for quantifying the interaction of test compounds and control compounds with each of the surfaces and assigning a numerical value characteristic of said quantified interaction of the test compound and each respective membrane surface. Typically, the screening system also includes a database comprising numerical values characteristic of the quantified interaction of selected control compounds or training sets of control compounds with the membrane surfaces. At least a portion of the selected control compounds have a predefined biological property. The system includes an analyzer (e.g. a programmable computer) for comparing the numerical values determined for the test compounds with the corresponding numerical values for control compounds and identifying control compounds having numerical values best matching those for the test compound. In one embodiment the system includes a graphics algorithm for displaying the numerical values for the test compound and the numerical values for at least a portion of the control compounds as visibly distinguishable vector quantities. In another embodiment the analyzer includes an algorithm using vector calculus manipulation to identify the control compound or compounds having numerical value best matching those of the test compound. Thus, for example, the system can be programmed to report all control compounds wherein Θ (see above) is less than 15°, more preferably less than 10°, or where $D^2$ is minimized and/or Q is maximized.

Figure 2:
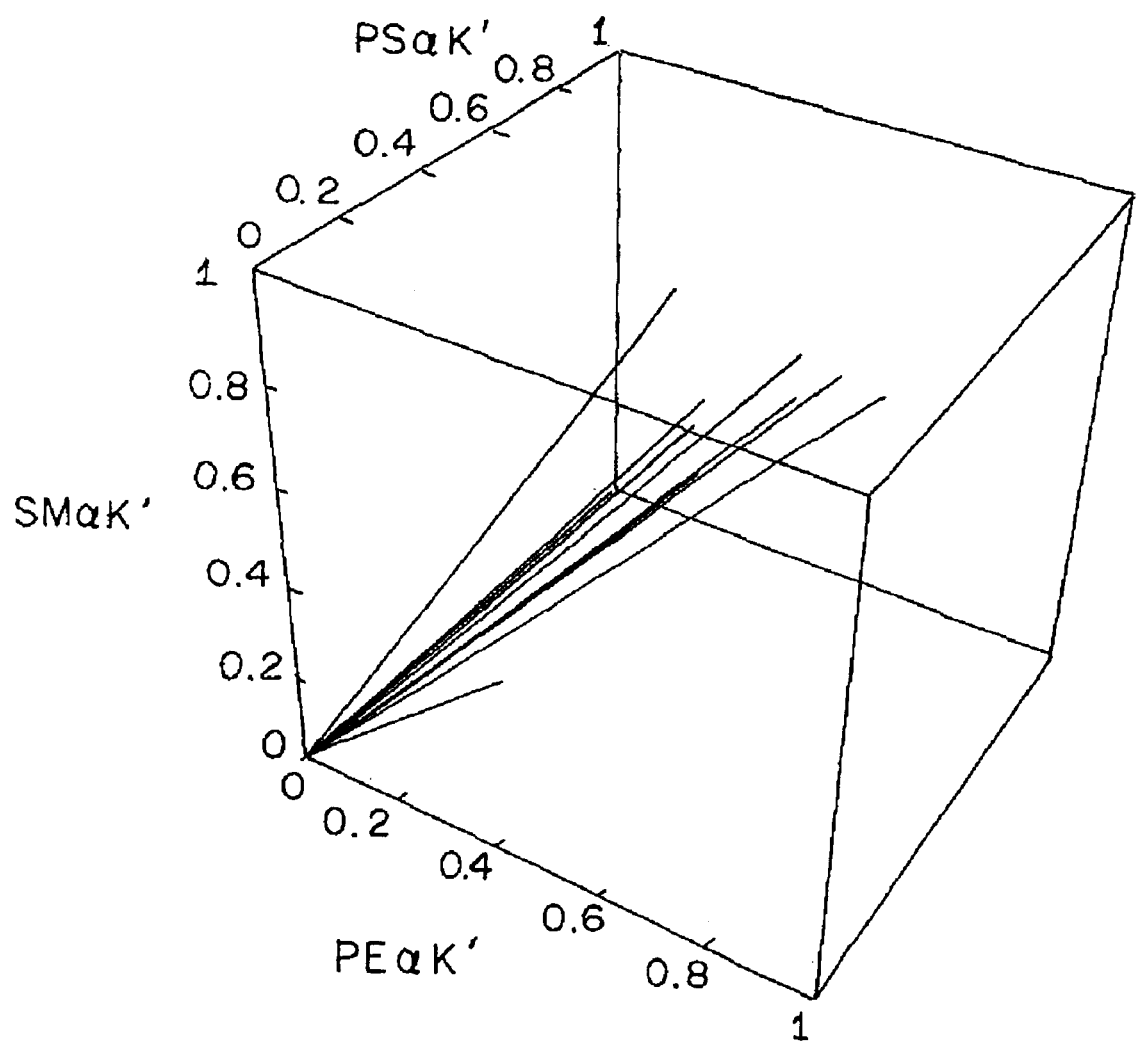
FIG. 2 is a 3-dimensional vector plot of membrane affinity data, for compounds known to act at dopamine receptors.

Generally speaking, it has been found that compounds of certain biological activities, exhibit relative membrane affinities such that their membrane binding data form a readily discernible grouping when presented as vectors in "membrane space". See FIGS. 1 and 2. FIG. 1 shows vector plots in 3-dimensional "membrane space" for compounds which act at serotonin receptors: buspirone, cinanserin, mescaline, methysergide, pIamphetamine, psilocin, quipazine, meterogline and others. FIG. 2 shows vector plots in 3-dimensional "membrane space" for compounds that act at dopamine receptors: apomorphine, clozapine, domperidone, haloperidol, pridinol, SCH23390, SKF38393, spiperone, sulpiride, chlorpromazine, dihyrexidine, dopamine, perphenazine, prochlorperazine.

That phenomenon (the grouping of membrane mimetic binding data as vectors in "membrane space") forms the basis of the present invention and allows multiple membrane binding constants to serve as a predictor of biological activity. While FIGS. 1 and 2 are illustrated as the products of pattern matching by vector analysis, other art-recognized mathematical analytical techniques such as multivariant analysis and principal component analysis can be applied to membrane binding data to compare test compounds with control compounds with known biological function. Vector analysis is particularly useful for pattern matching in accordance with this invention in that it can be carried out, albeit not graphically represented, in more than three dimensions. Such techniques can also be applied to data sets that include, in addition to data characteristic of multiple membrane affinities, other biologically significant molecular descriptors. Further, although membrane binding data acquisition is illustrated using immobilized artificial membrane chromatography supports in a high performance liquid chromatography system, other techniques can be used, for example, computer chips or similar devices with immobilized lipids, capillary zone electrophoresis columns coated with membrane lipids, Langmuir-Blodgett films, liposomes, and adsorbed monolayers of lipids on any surface, for example an AFM tip and evaluating the change in oscillation of the tip in the presence of test and control compounds. In addition to such empirical data acquisition techniques, numerical values characteristic of both MAF and non-MAF parameters can be obtained by computer calculations. Thus data sets for use in accordance with this invention can include calculated non-MAF parameters, and calculated MAF parameters including simulated MAF properties. "Calculated non-MAF parameters" as used in describing the present invention are numerical quantities that can be derived from a known chemical structure. Examples include surface area, polar surface area, number of H-bonds, topological indices, solubility, etc. These parameters alone do not predict the general membrane binding properties, i.e., MAFs, of compounds. The term "calculated MAF parameters" refers to a combination of calculated non-MAF parameters, with or without individual membrane binding constants, that can be used to predict Membrane Affinity Fingerprints (MAF). Since HPLC retention times can be used to calculate membrane binding constants, methods used to calculate retention times of solutes are actually calculating MAF parameters. An example of a calculated retention time for 12 compounds can be found in (Amie, D. Davidovic-Amie, D. Trinajstic, N., *J. Chem. Inf. Comput.* 1995, 35, 136–139.) The term "simulated MAF" refers to a calculated MAF parameter obtained from Molecular Dynamics Simulations of compounds with IAMs, bilayer membranes, other membrane mimetic surfaces, or a force field characteristic of these membranes.

In another embodiment of this invention there is provided novel carboxyl-functional, head group-protected phospholipids of the formula HOOC—W—OPO$_2$OZ wherein Z is protected glyceryl, 2-(protected amino ethyl), 2-protected carboxyl-2-aminoethyl, 2-protected carboxyl-2-protected amino ethyl or a readily cleavable protecting group, and W comprises the lipid residue of a biologically significant compounds such as sterols, steroids, and fatty acids including, for example, retinoic acid, or W comprises the lipid residue of other amphiphilic molecules found in natural biological membranes including, but not limited to lecithins, lysolecithins, cephalins, sphingomyelin, cardiolipin, glycolipids, gangliosides, and cerebrosides. Such compounds are useful for preparation of certain of the immobilized artificial membranes useful for comparing membrane interactions and predicting biological activities of test compounds. Alternatively W is the lipid residue of a phospholipid of the general formula W—OPO$_2$OB, wherein W can be acylglyceryl, diacylglyceryl, or N-acyl 3-O-(protected) sphingosin-1-yl, wherein "acyl" is $C_8$–$C_{24}$ alkanoyl or $C_8$–$C_{24}$ alkenoyl.

In another aspect of this invention novel carboxyl-functional, head group protected phospholipids of the formula HOOC—W—OPO$_2$OZ are prepared in high yield by phospholipase D (PLD) transphosphatidylation of compounds of the formula HOOC—W—OPO$_2$OCH$_2$CH$_2$N$^+$(CH$_3$)$_3$ in the presence of an excess of a protected alcohol of the formula ZOH wherein Z is protected glyceryl, 2-(protected amino)ethyl, 2-protected carboxyl-2-amino ethyl or the residue of an acid protecting group, for example, 4-nitrobenzyl or 4-nitrophenylethyl. W is a lipid reside as defined above with the proviso that it is selected so that the starting compounds serve as a substrate for phospholipase D activity. Typically about a 3-fold to a 15-fold stoichiometric excess of the alcohol is used, and the reaction is carried out in a buffered aqueous organic solvent, for example chloroform or ethyl acetate, in the presence of a water soluble calcium salt. The product carboxyl-functional compounds are useful for preparing novel head group-protected immobilized artificial membranes on surfaces of solid substrates having carboxyl reactive functional groups such as hydroxy, amino, and thiol groups. Removal of the protecting groups on the immobilized phospholipids provide the corresponding deprotected artificial membrane structures.

The term "protected" or "protecting group" as used in describing the present invention refers to those chemical moieties that 1) can be temporarily bonded to a reactive functional group (e.g., phospho, carboxyl, hydroxy or amino) to prevent subsequent unwanted reaction of the reactive functional group during other chemical modification of the compound bearing said functional group and that 2) can be removed from the functional group or groups at a subsequent synthesis step without unwanted reaction of other portions of the protected molecule. Protecting groups for amino, carboxyl and hydroxy functionalities are well known in the art, as are their respective synthesis and conditions for removal (deprotection). Preferred protected alcohols useful for the preparation of the carboxyl functional, head group-protected phospholipids in accordance with this invention are ispropylidene glycerol, allyl serine, 2-(t-butoxycarbonylamino)ethyl, 4-nitrobenzyl alcohol, and 2-(4-nitrophenyl)ethanol.

Another artificial membrane stationary phase useful for assessing membrane interaction and predicting biological properties in accordance with this invention is a novel immobilized ceramide-based membrane. In one embodiment the ceramide stationary phase is prepared by covalently bonding N-(13-carboxyltridecanoyl)-D-erythro-sphingosine through the ω-carboxyl group (via the ceramide-imidazolide) to silica propylamine and subsequent C-3 and C-10 endcapping of residual propylamine groups. The resulting stationary phase can be used in HPLC systems to predict skin permeability constants.

The immobilized artificial membranes used in accordance with this invention to predict biological activities can be prepared using one or more than one ω-carboxyl substituted lipids. Artificial membrane structures useful as a stationary phase for HPLC chromatographic determination of membrane interaction and having a predefined ratio or stoichiometry of phospholipid components can be prepared to simulate those lipid/phospholipid ratios known to exist in a predetermined biological membrane. Thus, the binding affinities of test compounds and control compounds to both homologous and heterologous membrane substrates can be measured and compared to assess/predict biological function.

Membrane binding data (numerical values relating to interaction with membranes or membrane mimetic surfaces) were obtained using HPLC chromatography on a multiplicity of membrane mimetic surfaces, preferably immobilized artificial membranes (IAMs). The membrane mimetic surfaces used to quantitate membrane lipid interactions were prepared from analogs of phosphatidylcholine (PC), phosphatidylserine (PS), phosphatidylethanolamine (PE), and sphingomyelin (SM). These membrane lipids were chosen because of their established asymmetry in plasma membranes. Synthetic methods for preparing immobilized membranes are well established. Experimentally, drugs were injected into high performance liquid chromatography (HPLC) columns. The peak positions in the chromatograms measure the affinity of compounds for the immobilized membrane lipid surfaces.

Comparing membrane binding properties among a multiplicity of compounds required a pattern matching process whereby the patterns being matched were sets of membrane binding data. Compounds with similar pharmacology have been found to cluster in membrane space. This supports the hypothesis that compounds with similar pharmacology have similar membrane binding properties. The dispersion of vectors among the compounds of a therapeutic class defines the region of membrane space where activity of that therapeutic class resides. When outliers in membrane space are observed for member of the class, other factors in addition to membrane binding may be critical for activity of the outlier. Overlap in membrane space among CNS compounds is consistent with these compounds exhibiting essential membrane binding properties needed for drug penetration through the blood brain barrier. Although active transport and efflux mechanisms have recently been emphasized as regulating penetration through the CNS, membrane binding must significantly contribute to the regulation of CNS transport because all CNS compounds tested have unique membrane binding compared to non-CNS compounds. The region occupied by non-CNS compounds differs from that of CNS compounds both in vector direction and vector magnitude. Thus, sets of membrane binding data can be used to determine if a given compound is likely to penetrate the blood brain barrier. Once CNS compounds penetrate the blood brain barrier and are free to distribute into different regions of the brain, membrane binding properties unique to each therapeutic class regulates the localization of compounds within the CNS. Specifically, when compound localization within the CNS is regulated primarily by membrane binding properties, then drug vectors within therapeutic classes are expected to occupy a unique region of membrane space. This clustering was observed for all therapeutic classes of compounds tested which suggests that the in vitro membrane binding model has significant utility in modeling the distribution of compounds within the CNS.

Vector plots in membrane space are useful for demonstrating that the angle between two drug vectors is small when compounds exhibit similar biological activities. However, angle calculations are not restricted to three membrane binding constants. Better grouping by therapeutic activity is attainable when more than three membrane binding constants are pattern matched. For instance, diazepam pattern matches membrane binding properties of anxiolytic compounds much better when four membrane binding constants are used for the analysis. As shown in Table 5, when only three membrane binding parameters were used for pattern matching diazepam to the database, only two anxiolytics were among the top ten compounds, whereas five anxiolytics were identified when four membrane binding parameters were used. Although larger angles are calculated when four verses three membrane parameters are used (Table 5), pattern matching membrane binding constants in N-dimensional membrane space appears to give better groupings of compounds regarding biological activity. The observation that compounds with biological activities different than diazepam are found in Table 5 emphasizes that overlap in membrane binding properties between different CNS therapeutic classes is unavoidable. In addition, the lack of a non CNS compound among the top ten matches in Table 5 emphasizes the clear distinction that exists between the membrane space occupied by CNS and non-CNS compounds.

steps, whereas, the use of PC-COOH to enzymatically prepare protected ω-carboxyl phospholipid ligands ($PL^{2\omega\text{-}COOH/P}$) from phospholipase D (PLD) reduced the total number of synthetic steps to ~20. The five $PL^{\omega\text{-}COOH/P}$ ligands prepared were analogs of phosphatidylglycerol ($PG^{2\omega\text{-}COOH/P}$, 1a), phosphatidylserine ($PS^{2\omega\text{-}COOH/P}$, 1b), phosphatidylethanolamine ($PE^{2\omega\text{-}COOH/P}$, 1c), phosphatidic acid ($PA^{2\omega\text{-}COOH/P}$, 1d) and sphingomyelin ($SM^{\omega\text{-}COOH/P}$, 2). PLD transphosphatidylation reactions using PC-COOH were typically ~90–95% complete. An interesting finding was that serine allyl ester was an excellent substrate for PLD and quantitative transphosphatidylation of PC-COOH with serine allyl ester was obtained. This is the first report describing the preparation of SM analogs suitable for bonding to molecular surfaces. $PL^{\omega\text{-}COOH/P}$ protecting groups were removed after bonding the ligands to silica propylamine and endcapping with straight chain anhydrides. After deprotection, five immobilized membrane surfaces were prepared that contain interfacial functional groups identical to PG, PA, PE, PS, and SM membrane lipids.

Although single chain ether PLs were previously used to prepare the first generation of IAM surfaces, two factors prohibited the wide spread use of ether lipids to prepare IAMs for measuring drug-membrane binding constants. One problem was that optimum predictions required immobilized lipids that are structurally similar to endogenous lipids found in cell membranes and single chain ether lipids lack several interfacial functional groups commonly found in the

TABLE 5

Pattern Matching Membrane Binding Constants in 3 Dimensions and 4 Dimensions. Angles were calculated from membrane binding data and are relative to the membrane binding data of diazepam. The Membrane Space for each analysis is given.

| Three Dimensional Pattern Matching Membrane Space = {PC, PE, PS} | | | Four Dimensional Pattern Matching Membrane Space = {PC, PE, PS, SM} | | |
| --- | --- | --- | --- | --- | --- |
| compound | angle | activity | activity | angle | compound |
| diazepam (ref. compound) | 0 | anxiolytic | anxiolytic | 0 | diazepam (ref. compound) |
| promethazine | 1.48 | depressant | anticonvulsants | 2.83 | nitrazepam |
| chlorodiazepoxide | 1.82 | anxiolytic | anxiolytic | 3.34 | chlorodiazepoxide |
| 2Br-LSD | 2.56 | LSD antagonist | LSD antagonist | 5.71 | 2Br-LSD |
| nitrazepam | 2.45 | anticonvulsant | anxiolytic | 5.77 | oxepam |
| procyclidine | 3.04 | nonCNS | antidepressant | 5.83 | R-deprenyl |
| prazepam | 3.16 | anxiolytic | anxiolytic | 6.48 | medzepam |
| cyclobenzaprine | 3.28 | psychosedative | hallucinogen | 7.38 | psilocin |
| imipramine | 3.44 | antidepressant | anxiolytic | 8.41 | prazepam |
| nefopam | 3.78 | antidepressant | anxiolytic | 10.15 | halazepam |

Synthesis of Ligands for Preparing Immobilized Artificial Membranes 1-myristoyl-2-(13-carboxytridecanoyl)-sn-3-phosphatidylcholine (PC-COOH) was used as a common chemical intermediate to prepare immobilized artificial membrane (IAM) surfaces for measuring drug-membrane interactions. Previous preparation of IAMs containing PC, PG, PA, PE, and PS from ether phospholipids required ~30 majority of membrane phospholipids. The second problem was that ether PLs required numerous synthetic steps and the preparation costs are high. Accordingly, in another embodiment of the invention efficient synthetic strategies were developed to prepare carboxyl analogs of membrane phospholipids for immobilization that bear identical interfacial functional groups as those found in the PLs forming the cell membranes.

Scheme 1

Structures of protected diacylated phospholipid analogs of PG, PA, PE and PS. After immobilization and following deprotection, these ester PLs have identical interfacial functional groups to endogenous membrane phospholipids (PG, PA, PE, or PS).

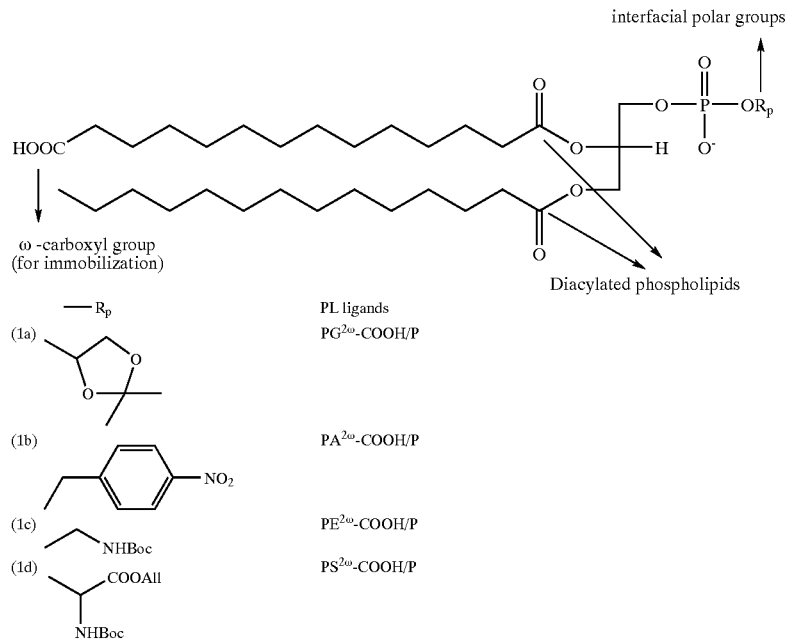

Scheme 1 shows the protected diacylated $PL^{2\omega\text{-}COOH/P}$ ligands prepared during this work. The protecting groups, $R_P$, shown in Scheme 1 are the same protecting groups used to prepare single chain ether PLs that were immobilized except for the serine analog. Ether PLs containing serine carboxyl were protected with a tert-butyl ester, whereas the present synthetic procedure used an allyl ester group because this protecting group does not interfere with PLD transphosphatidylation reactions. Scheme 2 shows the carboxyl SM analog (2) prepared as well as the main structural differences between $SM^{\omega\text{-}COOH/P}$ and $PL^{2\omega\text{-}COOH/P}$ ligands. The $SM^{\omega\text{-}COOH/P}$ ligand was used to prepare an IAM surface that model drug binding to endogenous membranes enriched in SM; an example is the kidney brush border cells where 80% of SM in the plasma membrane is located in the outside membrane leaflet.

Scheme 2

Structure of w-carboxyl sphingomyelin analog. The main structural differences between it and ester PLs are labeled.

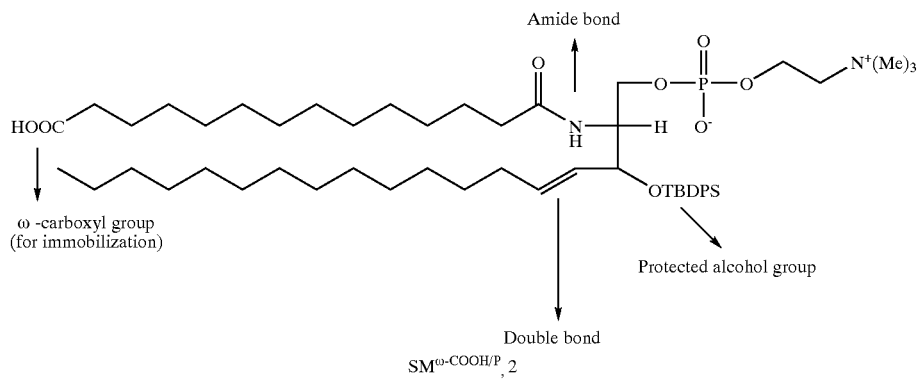

SCHEME 3

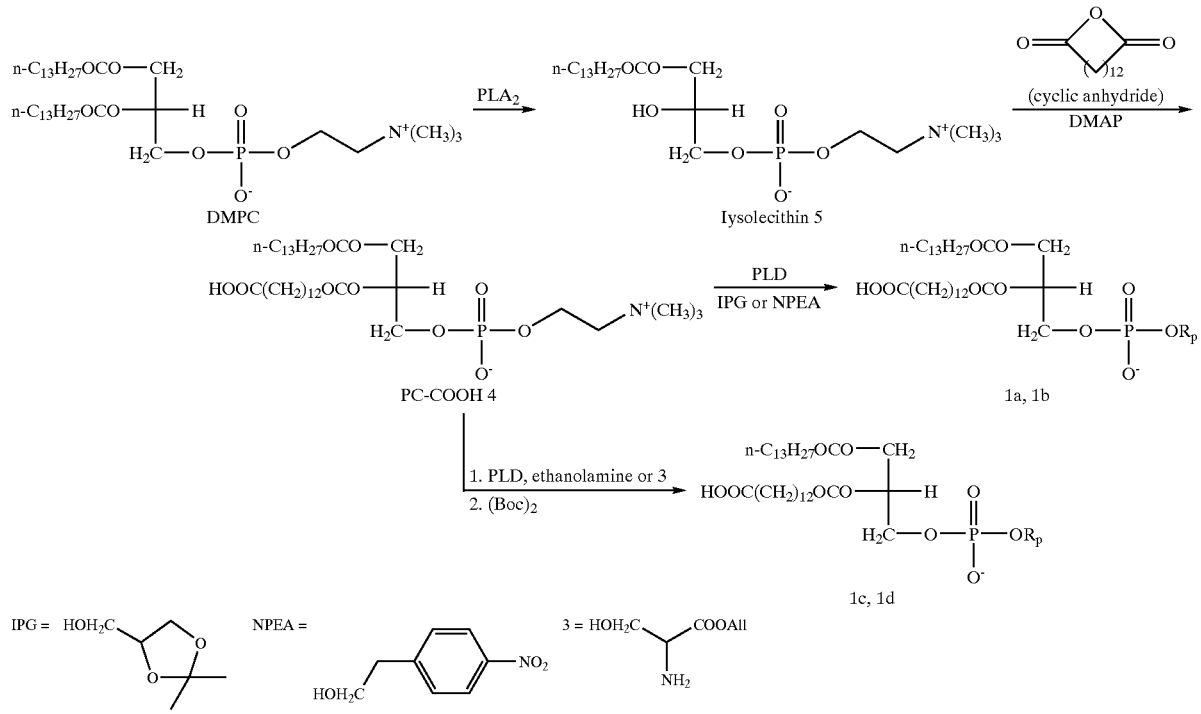

The general synthetic route to prepare double chain ester PLs, instead of single chain ether PLs, bearing ω-carboxyl groups is shown in Scheme 3. PLA$_2$ hydrolysis of DMPC to obtain lysolecithin (5) was found to be quantitative but reaction conditions are enzyme specific. In addition, PLA$_2$s from different manufacturing lots contain different contaminants that interfere with product formation. Several PLA$_2$s including Naja mocambique mocambique PLA$_2$ (pI=8.8), Naja mocambique mocambique PLA$_2$ acidic isoenzyme and bee venom PLA$_2$ (*Apis mellifera*) were tested for this work and all enzymes could be used to obtain quantitative hydrolysis of DMPC, but, reaction conditions needed to be optimized for each enzyme. Bee venom PLA$_2$ was reported to have high activity in low water-organic solvent systems (1.7% buffer/chloroform V/V). Preliminary studies were intended to determine if 1.7% V/V buffer/CHCl$_3$ was sufficient for scale up reactions whereby several gram quantities of 5 could be produced from a single reaction. The first reaction was a 100 fold scale up from the published procedure and Tris buffer was used instead of HEPES. DMPC (1.0 g) incubated with bee venom PLA$_2$ (1000 units) in 1.7% V/V Tris buffer (50 mM, pH 7.2)/CHCl$_3$ did not react over 4 hours, and when the aqueous phase was adjusted to 5% V/V buffer/CHCl$_3$ the reaction still did not proceed. Only when 10% V/V buffer/CHCl$_3$ conditions were used did the reaction proceed to completion in ~6 hours. Product precipitation in acetone always resulted in large amounts of the buffer reagent contaminating 5. For this reason, reactions were investigated to identify an acetone soluble buffer that does not interfere with PLA$_2$ cleavage of phospholipids. Triethanolamine buffer was found to be acetone soluble and permitted PLA$_2$ hydrolysis of DMPC reactions to proceed quantitatively to generate lysolecithin (5). It was found that in triethanolamine buffer, Naja mocambique mocambique PLA$_2$ (pI=8.8) had the highest efficiency for DMPC hydrolysis among the enzymes tested which included Naja mocambique mocambique PLA$_2$ acidic isoenzyme and bee venom PLA$_2$ (*Apis mellifera*). Lysolecithin purification required three acetone precipitations. Several PCs were also hydrolyzed in quantitative yields using PLA$_2$ indicating the procedure may be used as a general synthetic step for obtaining lysophosphatidylcholine intermediates.

PC-COOH (4) was prepared from 5 as described. Earlier studies indicated that PLD from either vegetables or microbacterials has activity in organic/aqueous systems and it accepts unnatural substrates (including both primary and secondary alcohols) and generates phosphoester products. Therefore we extended PLD transphosphatidylation reactions to prepare the final ligands 1a–1d (Scheme 1). Ligands 1a and 1b were prepared directly from PLD and did not require additional headgroup protection steps prior to ligand immobilization. In contrast, ligands 1c and 1d require additional synthetic steps to protect the primary amines on each of these compounds so that these amines do not interfere with immobilization of the PL$^{2\omega\text{-}COOH/P}$ ligands. The major side product in PLD reactions is the formation of PA because water is an efficient competitor to the alcohols used for the PLD reactions. Thus one of the primary goals during PLD reactions is to minimize formation of PA side products regardless of PC analog subject to PLD transphosphatidylation. Based on TLC, PLD reactions using compound 4 show either no or trace amounts of PA-COOH.

Commercially available IPG alcohol was used to prepare PG$^{2\omega\text{-}COOH/P}$ (1a) by PLD transphosphatidylation; the reaction was facile and an ~83.2% yield was obtained after product purification by flash chromatography. The PLD reaction was >90% complete and product recovery was decreased due to column chromatography. No PA side product formed during the reaction conditions used for PLD conversion of compound 4 to the ligand 1a. Although compound 4 is not very soluble in buffer/ethyl acetate solvents, the yield of PG$^{2\omega\text{-}COOH/P}$ was much higher and the reaction times was much shorter, in this mixed solvent system compared to buffer/CHCl$_3$ solvent system. Similar observations were found for the PLD transphosphatidylation reactions using compound 4 and ethanolamine which was the alcohol used to prepare PE$^{2\omega\text{-}COOH/P}$ (1c).

The most important consideration when using PLD enzymology to prepare PS$^{2\omega\text{-}COOH/P}$ (1d) is the presence of both the serine carboxyl group and the $\omega$-carboxyl group located on the terminal part of the acyl chain which is used for immobilization of the ligand. The serine carboxyl group must be protected prior to PLD reactions so that the $\omega$-carboxyl remains free and can be used for immobilization. However, after immobilization the serine carboxyl protecting group must be removed using solution conditions that do not degrade the immobilized membrane surface. PLD reactions using serine methyl ester, cannot be used because conditions for deprotecting the serine methyl ester will also hydrolyze the interfacial esters of the immobilized lipids.

Thus a specific protecting group for the serine carboxyl had to be identified that permits not only the PLD transphosphatidylation to proceed efficiently, but, the protecting group must be able to be removed under mild deprotection conditions to generate the free serine carboxyl after immobilization. Thus synthetic strategies for preparing the ligand 1d by PLD enzymology tested serine benzyl ester, phenacyl ester and allyl ester. All of these esters can be removed under mild solution conditions. Steric hindrance of benzyl alcohol and 2-hydroxyacetophenone caused these alcohols to be poor substrates for PLD. However, serine allyl ester underwent quantitative PLD transphosphatidylation and this chemical intermediate was not purified; the unreacted serine amine was directly protected with Boc to form the ligand 1d which is suitable for immobilization. After immobilization, allyl ester can be removed using tributyltin hydride (Bu$_3$SnH) and the catalyst bis(triphenylphosphine) palladium (II) chloride PdCl$_2$(PPH$_3$)$_3$. The one pot two step reaction from compound 4 to PS$^{2\omega\text{-}COOH/P}$ (1d) had a overall yield of 87.1% after the product was purified by column chromatography. The reason for not protecting the serine amine prior to PLD reaction is that a free amino is usually needed for serene to be a good substrate for PLD enzymes.

The preparation of SM$^{\omega\text{-}COOH/P}$ (2) (see Scheme 4) ligand involved aminolysis of endogenous SM to form sphingosine-1-phosphocholine with a free amine. Prior to reacting the free amine with a large ring cyclic anhydride, the alkylic alcohol was protected with tert-butyldiphenylsilane (TBDPS). The TBDPS protecting groups can be removed with TBAF which does not degrade the silica surface after the ligand 2 is bonded to silica.

The ester ligands were bonded to silica surfaces similar to procedures previously developed in our laboratory. See U.S. Pat. No. 4,931,498. Typically IAMs are prepared from 3 sequential bonding processes. The first bonding process links the PL$^{\omega\text{-}COOH/P}$ ligands to the surface using CDI as the activation agent and FTIR spectroscopy is used to verify that the headgroup protecting groups remain intact during the immobilization process. Residual amines on the silica surface are then endcapped with alkyl anhydrides.

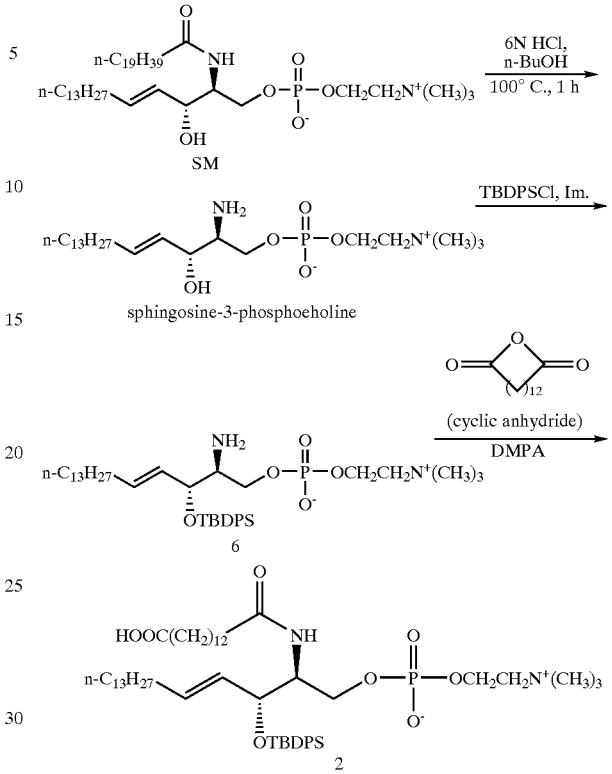

SCHEME 4

A detailed study of endcapping reactions has been performed, and the results from this and other work indicate that either long chain or short chain anhydrides can be used for endcapping. However, a critical concept is that the endcapping reactions are performed until the surfaces are ninhydrin negative. Typically, decanoic (10) anhydride is the first endcapping reagent followed by propionic (C3) anhydride. However, double endcapping with C3 or C10 or any other combination can be performed depending on the use of the IAM packing materials. For instance, NMR studies of the IAMs require that the IAMs suspend in D$_2$O which can only be achieved by omitting the endcapping with C10 anhydrides. Thus endcapping is not routine from a synthetic perspective because it can be used to control the hydrophobicity, wettability, and other properties of the final surfaces.

Since both endcapping may be varied and the protection groups vary among PL$^{2\omega\text{-}COOH/P}$ ligands, a nomenclature is needed to identify the chemical surface intermediates formed throughout the multistep bonding process. PL$^{2\omega\text{-}COOH/P}$ ligands are always bonded to the silica surface first, followed by endcapping and deprotection. The nomenclature throughout the sequential bonding processes for preparing the $^{ester}$IAM.PS$^{C3/C3}$ surface (10) was as follows:

SPA→$^{ester}$IAM.PS$^{P}$→$^{ester}$IAM.PS$^{P/C3}$→$^{ester}$IAM.PS$^{P/C3/C3}$→$^{ester}$IAM.PS$^{C3/C3}$ (10)

where SPA is silica propylamine starting material which becomes $^{ester}$IAM.PS$^{P}$ after immobilizing PS$^{2\omega\text{-}COOH/P}$, which then becomes $^{ester}$IAM.PS$^{P/C3/C3}$ after two sequential endcapping steps using C3 anhydride. The superscript p indicates that serine protecting groups have not been removed. After removal of all the protecting groups, $^{ester}$IAM.PS$^{P/C3/C3}$ becomes the final product 10. This nomenclature, which is exemplified for the preparation of $^{ester}$IAM.PS$^{C3/C3}$ surfaces, is used for all IAMs.

Bonding strategies of the $PL^{2\omega\text{-}COOH/P}$ ligands to the silica surfaces were the same as that of PC-COOH which did not require protecting groups. However, the $PL^{2\omega\text{-}COOH/P}$ ligands are less soluble in $CHCl_3$ than PC-COOH which caused longer CDI activation times. The CDI activated $PL^{2\omega\text{-}COOH/P}$ ligands are very soluble and bonding to silica propylamine was facile. When ether PLs were used for preparing IAMs aqueous HCl was used to deprotect Boc, tert-butyl esters, and isopropylidene (IPG) groups because the immobilized ether lipids were stable to this reaction condition. However, the ester PLs described in this report are susceptible to acid hydrolysis and we used anhydrous TFA to remove acid sensitive protecting groups.

We have found that the only way to monitor trace amounts of functional groups on the IAM surface after the $PL^{2\omega\text{-}COOH/P}$ ligands are immobilized is to use IR microscopy. However compared to all other protecting groups tested, direct monitoring the deprotection of the allyl ester groups on $^{ester}IAM.PS^{P/C3/C3}$ by IR microscopy was impassible because allyl ester group does not have an IR band in a unique region of IR spectrum. From peptide chemistry, deprotection of allylic groups are quantitative using tributyltin hydride. Nevertheless the deprotection was essential to monitor because interfacial surface chemistry significantly affects many chemical reactions and deprotection of allyl ester may not be facile on IAM surfaces.

IR band shifts with serine carboxyl group on $^{ester}IAM.PS^{C3/C3}$ in the IR spectra under acidic and basic conditions were used to monitor the extent of deprotection. Thus after deprotecting $^{ester}IAM.PS^{P/C3/C3}$ with $Bu_3SnH$ and $PdCl_2$, $PPh_3)_3$, IR spectra of the acidified IAM surface (serine-COOH) and basified IAM surface (serine-COO$^-$) showed a decrease in the integrated ester region between 1780–1680 cm$^{-1}$ by ~1.3 fold. This decrease in intensity was expected because the surface contains two interfacial esters from the immobilized phospholipid. The serine carboxyl shift from 1710 cm$^{-1}$ to 1550 cm$^{-1}$ when the serine COOH is ionized to serine COO$^-$ chemical species moved the deprotected functional group to a new region of the IR spectra allowing the deprotection reaction to be monitored.

Numerous synthetic strategies can be developed to prepare the assortment of ester $PL^{2\omega\text{-}COOH/P}$ ligands shown in Scheme 1. For instance, $PLA_2$ hydrolysis of endogenous phospholipids including PG, PA, PE, PS can be performed followed by protecting polar headgroups and linking a long chain acyl group with an $\omega$-carboxyl group. This type of synthetic strategy whereby each $PL^{2\omega\text{-}COOH/P}$ ligand is synthesized from an endogenous precursor has several disadvantages, the most obvious of which is the generation of several extra synthetic steps to obtain all $PL^{2\omega\text{-}COOH/P}$ ligands.

However, equally important considerations are (1) endogenous starting materials like PG, PA, PE, and PS are expensive, and (2) the lysophospholipids of PG, PA, PE, and PS have poor solubility in aprotic solvents which makes them difficult to undergo following synthetic chemical reactions. The selection of PC-COOH (4) as a common intermediate (Scheme 3) to prepare ester $PL^{2\omega\text{-}COOH/P}$ thus avoids the usage of expensive starting materials PG, PA, PE, and PS and eliminates lysophospholipid intermediates. The synthetic strategy described herein is efficient for both small and large scale reactions and will be generally useful for preparing membrane surfaces. The ligands can be bonded to any molecular surface.

General Experimental Procedures 1,2-dimyristoylcholine-sn-glycero-3-phosphocholine (DMPC) was bought from Genzyme Pharmaceuticals (Cambridge, Mass.). Bee venom $PLA_2$ (*Apis mellifera*), Naja mocambique mocambique $PLA_2$ (pI=8.8), Naja mocambique mocambique $PLA_2$ acidic isozyme, PLD (from Streptomyces species), $CaCl_2.2H_2O$ and ethanolamine were ordered from Sigma Chemical Co. (St. Louis, Mo.). Triethanolamine (TEA), tris(hydroxymethyl)aminomethane (Tris), ethylenediaminetetraacetic acid disodium salt (EDTA), anhydrous trifluoroacetic acid (TFA), 1,-1-carbonyldiimidazole (CDI), propionic anhydride (C3), decanoic anhydride (C10), tributyltin hydride ($Bu_3SnH$), bis(triphenylphosphine)palladium (II) chloride ($PdCl_2$ $(PPh_3)_3$), alcohol-free anhydrous chloroform (stabilized with amylene), methylene chloride, 4-dimethylaminopyridine (DMAP), sodium acetate, di-tert-butyl dicarbonate (Boc anhydride), p-nitrophenethyl alcohol (NPEA), triethylamine, tert-butyldiphenylsilyl chloride (TBDPSCl), imidazole, n-butanol, 1,12-dodecanedicarboxylic acid, tetrabutylammonium fluoride (TBAF) and allyl bromide were purchased from Aldrich (Milwaukee, Wis.). Sphingomyelin (brain) and eggPC were ordered from Avanti Polar Lipids, Inc. (Alabaster, Ala.). Deuterated solvents for NMR spectroscopy including methanol and chloroform were from Cambridge Isotope Laboratories, Inc. (Andover, Mass.) Chloroform (alcohol free), acetone, isopropylalcohol, methanol, acetone, hexane, ethyl acetate, acetic acid, hydrochloride and sodium hydroxide were from Mallincrodt, Inc. (Paris, N.Y.). Labmotor, stirring shaft and stirrer blades were purchased from ACE Glass, Inc. (Louisville, Ky.). Phospray reagent used for detecting phosphorus-containing organic compounds and ninhydrin reagent used for detecting amine-containing compounds were ordered from Supelco, Inc. (Bellefonte, Pa.). Silica propylamine (SPA) was provided by Rockland Technologies Inc. (Newport, Del.). SPA (RN39-94) was used to prepare $^{ester}IAM.PL$ surfaces and it is trifunctional and has a surface area of 180 m$^2$/g and a pore size of 80 Angstroms. The density of propylamine groups on RN39-94 is 3.09 $\mu$mol/m$^2$. SPA (RN38-94) was used to prepare IAM.SM surfaces and it is monofunctional and has the same surface area and pore size as RN39-94. The density of propylamine groups on RN38-94 is 2.06 $\mu$g/m$^2$. All infrared spectrum were recorded on a Nicolet magna-IR spectrometer interfaced with a IR Plan I microscope. Elemental analysis was performed on a Perkin-Elmer PE 240 in the Microanalytical Laboratory at the Purdue University Chemistry Department using approximately 10–15 mg of IAMs.

1-myristoyl-sn-2-hydroxyphosphatidylcholine (5, lysolecithin)

DMPC (10.0 g) was weighed and dissolved in chloroform (306 ml). Then 32.0 ml of 50 mM TEA (pH 7.2) buffer containing 2.5 mM Ca$^{++}$ and 0.25 mM EDTA was added. Naja mocambique mocambique $PLA_2$ enzyme solution (1 ml, 1,000 units/ml in 50 mM TEA buffer) was pipetted into the DMPC suspension. The viscous white reaction was paddle-stirred at 100 rpm for either 7.5 hours (basic isozyme) or 11.0 hours (acidic isozyme). Isopropylalcohol (100 ml) was added to the reaction mixture before rotoevaporation to avoid bubbling during solvent removal. After rotoevaporation, the residue was suspended in methanol (100 ml) and sonicated (1~2 min) to solubilize the residue. The methanol solution containing product was slowly pipetted into acetone (~500 ml) which caused a white precipitate (the product) to immediately form.

Complete precipitation required overnight incubation at 4° C. The precipitated product was collected by filtration using an F glass-sintered filter. TLC ($CHCl_3/CH_3OH/H_2O$= 65:35:4) showed trace amounts of myristic acid and TEA were contaminating the lysolecithin product and a second precipitation was needed to obtain 5 that did not contain any traces of myristic acid. A third precipitation with the pH adjusted to 9.7 completely removed the TEA from the product and pure compound 5 (5.16 g, 73.1%) was obtained after vacuum dry overnight. Recovery of lysolecithin from the 3rd filtrate by an additional precipitation increased the yield to ~80.0%. This reaction was performed ~50 times to obtain 285 g of lysolecithin which was used to prepare PC-COOH (4) by an established procedure. TLC in $CHCl_3$/$CH_3OH$/$H_2O$ (65:25:4) showed a pure product (Rf=0.34); FTIR: (thin film, $cm^{-1}$) 2955.24, 2917.03, 2849.68, 1734.22, 1467.66, 1234.61, 1086.39, 1056.77. $^1H$ NMR (300 MHz, $CDCl_3$, δ ppm): FAB-MS [M+H$^+$] calcd for $C_{22}H_{46}O_7PN$ 468.6, found 468.5.

1-Myristoyl-2-(13-carboxytridecanoyl)-sn-3-phosphatidylcholine (4, PC-COOH)

L-serine allyl ester (3)

N-(tert-butoxycarbonyl)-L-serine (25 g) was suspended in anhydrous ethyl acetate (600 ml) using a r. b. flask (1000 ml) and then allyl bromide (60 ml) and triethylamine (24 ml) were added. After stirring for 24 hours, the reaction mixture was filtered, and the filtrate was concentrated via rotoevaporation to yield a yellow oil. The crude product was purified by flash chromatography using a step hexane/ethyl acetate gradient from hexane (500 ml) followed by hexane/ethyl acetate (4:1, 1000 ml), hexane/ethyl acetate (2:1, 1000 ml), and hexane/ethyl acetate (1:1, 1000 ml). After drying in a vacuum oven overnight, 27.2 g of the intermediate N-tert-butoxycarbonyl-L-serine allyl ester was obtained (93% yield). TLC in ethyl acetate/hexane (1:1) showed a pure product (Rf=0.39); FTIR: (thin film, $cm^{-1}$) 3415.86, 2978.14, 2933.60, 2886.66, 1743.43, 1715.75, 1512.33, 1392.96, 1370.85, 1342.40, 1165.13, 1060.54. $^1H$ NMR (300 MHz, $CDCl_3$, δ ppm): 5.87 (1H, m), 5.54 (1H, d, J=7.79 Hz), 5.28 (1H, d, J=17.17 Hz), 5.20 (1H, d, J=10.40 Hz), 4.61 (2H, d, J=5.62 Hz), 3.87 (2H, m), 1.40 (9H, s). CI-MS [M+H$^+$] calcd for $C_{11}H_{19}NO_5$ 246.3, found 246.0.

N-tert-butoxycarbonyl-L-serine allyl ester (27.2 g) was placed in a 500 ml r. b. flask and cooled to 0° C. To this yellow oil, 50% TFA/$CH_2Cl_2$ (100 ml) was added under positive $N_2$ pressure. The reaction mixture was stirred at 0° C. (30 min), warmed to room temperature, and stirred for 2 h. TFA and $CH_2Cl_2$ were removed by rotoevaporation to yield a yellow oil. The yellow oil was dissolved in ether (200 ml). After 3 h at 4° C., the product completely precipitated. The precipitated product was collected by filtration and washed with ether (50 ml) and hexane (20 ml). The white precipitate was dried in a vacuum oven overnight. Dry L-serine allyl ester (3) was obtained (15.6 g, 100% yield). TLC in $CH_2Cl_2$/$CH_3OH$/$H_2O$ (65:25:4) showed a pure product (Rf=0.58). FTIR: (thin film, $cm^{-1}$) 2994.54, 2960.64, 2891.49, 1747.28, 1674.06, 1201.52, 11.45.92. $^1H$ NMR (300 MHz, $CDCl_3$, δ ppm): 5.86 (1H, m), 5.30 (2H, m), 4.59 (2H, d, J=6.43 Hz), 4.09 (2H, m), 3.77 (1H, m). FAB-MS [M+H$^+$] calcd for $C_6H_{11}NO_3$ 146.2, found 146.0.

3-O-(tert-butyldiphenylsilyl)-sphingosine-1-phosphocholine (6)

Sphingosine-1-phosphocholine was prepared by hydrolysis of SM with minor modification. Briefly, a solution of SM (10.5 g, 15 mmol), n-BuOH (150 ml), and HCl (45 ml, 6.0 N) was stirred at 100° C. for 1 hour followed by rotoevaporation and vacuum drying. The sphingosine-1-phosphocholine product was not purified, but, product formation was verified by FAB-MS m/z 465.2 [M+H$^+$]. Sphingosine-1-phosphocholine was dissolved in THF (500 ml) followed by the addition of TBDPSCl (23.4 ml, 90 mmol) and imidole (12.2 g, 90 mmol) in that order. The reaction was stirred (40° C., 10 h) followed by rotoevaporation and purification by column flash chromatography. A white solid (5.64, overall yield 53%) was obtained after column chromatography. TLC in $CHCl_3$/$CH_3OH$/$H_2O$ (65:25:4) showed a pure product (Rf=0.25). FTIR: (thin film, $cm^{-1}$) 3390.56, 3071.58, 3046.65, 3015.28, 2956.99, 2925.18, 2854.48, 1963.80, 1898.78, 1830.79, 1620.98, 1428.53, 1239.36, 1059.06, 973.34. $^1H$ NMR (300 MHz, $CDCl_3$, δ ppm): 7.66 (4H, m), 7.32 (6H, m), 5.43–5.09 (2H, m), 4.45 (3H, m), 4.12 (4H, m), 3.40 (9H, s), 3.39 (1H, m), 1.64 (2H, m), 1.24 (22H, m, br s), 1.00 (9H, s), 0.86 (3H, tr, J=6.45 Hz). FAB-MS [M+H$^+$] calcd for $C_{39}H_{67}N_2O_5PSi$ 703.1, found 703.2.

3-O-(tert-butyldiphenylsilyl)-sphingomyelin (2, $SM^{\omega\text{-}COOH/P}$)

A 200 ml solution of 6 (5 g, 7.1 mmol) and 1,12-dodecanedicarboxylic anhydride (prepared from 1,12-dodecanedicarboxylic acid (5.0 g, 19.35 mmol) and DCC (4.0 g, 19.39 mmol) as described [Pidgeon, 1989 #8]) was stirred at r.t. for 10 hours. The reaction solvent was removed by rotoevaporation and product was purified using a step gradient mobile phases consisting of $CH_2Cl_2$ (500 ml), $CH_2Cl_2$/THF (1:1, 500 ml), $CH_2Cl_2$/$CH_3OH$ (1:1, 1000 ml), and $CH_2Cl_2$/$CH_3OH$/$H_2O$ (65:35:4, 3000 ml). The chromatography fractions containing the product were pooled, and after rotoevaporation and vacuum oven drying 5.4 g of $SM^{\omega\text{-}COOH/P}$ (2) was obtained (80.6% yield). TLC in $CHCl_3$/$CH_3OH$/$H_2O$ (65:25:4) showed a pure product (Rf= 0.47). FTIR: (thin film, $cm^{-1}$) 3312.05, 3071.70, 3046.10, 2923.61, 2855.04, 1960.21, 1899.87, 1831.31, 1742.70, 1703.39, 1660.42, 1546.28, 1466.74, 1428.35, 1065.80, 967.63. $^1H$ NMR (500 MHz, $CDCl_3$, δ ppm): 7.64 (4H, m), 7.34 (6H, m), 5.34–5.04 (2H, m), 4.39 (1H, dd), 4.24 (2H, m), 4.02 (2H, m), 3.68 (3H, m), 3.21 (9H, s), 2.30–1.92 (4H, m), 1.76–1.37 (6H, m), 1.24 (38H, br s), 1.04–1.00 (9H, 3 s), 0.84 (3H, tr, J=6.56 Hz). FAB-MS [M+H$^+$] calcd for $C_{53}H_{91}N_2O_8PSi$ 943.4, found 943.0.

1-Myristoyl-2-(13-carboxytridecanoyl)-sn-3-phosphatidylglycerol-2'-3'-isopropylidene (1a, $PG^{2\omega\text{-}COOH/P}$)

PC-COOH (1.01 g, 1.43 mmol) was weighed and suspended in ethyl acetate (56 ml) and sonicated (5 min). The suspension was stirred (30° C., 15 min) before pipetting 10.62 ml of NaOAc buffer (composed of 100 mM NaOAc and 50 mM $CaCl_2$, pH 6.5) and 1.6 ml (12.10 mmol) of (R)-isopropylidene glycerol (IPG). After addition of IPG, the two-phase system immediately emulsified. PLD (100 μl, 1.0 unit/μl in NaOAc buffer) was added and the reaction monitored by TLC ($CHCl_3$:$CH_3OH$:$NH_3$.$H_2O$=65:25:4), after 2 h>60% of the PC-COOH was converted to $PG^{2\omega\text{-}COOH/P}$. Additional PLD (40 μl) was added and the reaction incubated for another 5 hours (90% completion based on TLC). The reaction mixture was acidified using $KHSO_4$ (1 M, 1.0 ml), then concentrated by rotoevaporation and the resulting residue was purified by flash chromatography using $CHCl_3$/$CH_3OH$/$H_2O$=65:25:3. Chromatography fractions containing product were pooled, concentrated by rotoevaporated and vacuum dried; the yield after column chromatography was 1.74 g of a white solid (83.2% yield). TLC in $CHCl_3$/$CH_3OH$/$H_2O$ (65:25:4) showed a pure product (Rf=0.40). FTIR: (thin film, $cm^{-1}$) 2982.51, 2923.36, 2852.97, 1741.51, 1710.84, 1556.64, 1462.17, 1415.60, 1379.37, 1370.00, 1244.68, 1219.69, 1160.35, 1106.00, 1069.15. $^1H$ NMR (500 MHz, $CDCl_3$, δ ppm): 5.24 (1H, br, m), 4.37 (1H, br, m), 4.29 (1H, br, m), 4.17 (2H, br, m), 4.04 (3H, br, m), 3.90 (1H, br, m), 3.80 (1H), 2.29 (6H, m), 1.57

(6H, m), 1.42 and 1.35 (3H, s, —CC$\underline{H}_3$, one of the two conformers), 1.40 and 1.33 (3H, s, —CC$\underline{H}_3$, one of the two conformers), 1.26 (36H, m), 0.86 (3H, t, J=7.00 Hz). FAB-MS [M+H$^+$] calcd for $C_{37}H_{69}O_{12}P$ 737.9, found 737.5.

1-myristoyl-2-(13-carboxytridecanoyl)-sn-3-phosphatidyl-p-nitrophenylethanol (1b, $PA^{2\omega\text{-}COOH/P}$)

$PA^{2\omega\text{-}COOH/P}$ was prepared similar to $PG^{2\omega\text{-}COOH/P}$ except that p-nitrophenethyl alcohol was used instead of IPG for the PLD transphosphatidylation reaction and the reaction was scale up by 1.5 fold. Optimum yields required PLD (1.0 unit/µl) to be sequentially added in three increments: 100 µl, 2 h incubation; 37 µl, 2 h incubation; then 50 µl-PLD, incubation for 12 hours). The product was both phospray positive and UV positive. The reaction mixture was acidified with KHSO$_4$, (1.042 ml of 1M), concentrated by rotoevaporation and the product purified by flash chromatography using silica gel. The solvent system was 700 ml of CHCl$_3$/CH$_3$OH (9:1) followed by 800 ml of CHCl$_3$/CH$_3$OH/H$_2$O (65:25:3) Chromatography fractions containing product were pooled, concentrated by rotoevaporated and vacuum dried; the yield after chromatography was 1.12 g of light yellow solid (75.1% yield). TLC in CHCl$_3$/CH$_3$OH/H$_2$O (65:25:4) showed a pure product (Rf=0.42). FTIR: (thin film, cm$^{-1}$) 2923.70, 2852.81, 1740.44, 1705.13, 1603.81, 1550.54, 1522.11, 1465.95, 1345.88, 1220.07, 1108.70, 1070.67, 1034.59. FAB-MS [M+H$^+$] calcd for $C_{39}H_{66}NO_{12}P$ 772.9, found 777.5.

N-tert-Butyloxycarbonyl-1-myristoyl-2-(13-carboxytridecanoyl)-sn-3-phosphatidylethanolamine (1c, $PE^{2\omega\text{-}COOH/P}$)

$PE^{2\omega\text{-}COOH/P}$ was prepared similar to $PG^{2\omega\text{-}COOH/P}$ except that a mixed solvent system, ethyl acetate/chloroform (4.6:1) was used. Chloroform was alcohol free. Based on scanning densitometry of TLC plates developed in CHCl$_3$:CH$_3$OH:NH$_3$.H$_2$O (65:25:4), ~88.0% of PC-COOH starting material was converted to the corresponding PE carboxyl analog. The reaction mixture was concentrated by rotoevaporation and the intermediate was not purified prior to protecting the primary PE amine with Boc. To the concentrated residue, Na$_2$CO$_3$ (20 ml, 1.0 M) and dioxane (40 ml) were added. The reaction mixture was cooled to 0° C. before adding (Boc)$_2$O (1.98 g, 9.07 mmol). The reaction was stirred (0° C., 1 h), r.t. for 3 hours followed by acidification by KHSO$_4$ (40 ml, 1.0 M). Addition of chloroform (40 ml) caused the milky emulsions reaction mixture to form two layers. The organic layer was collected and combined with the chloroform washings (2×40 ml) of the aqueous layer. The chloroform extractions were concentrated by rotoevaporation before purification of the product using silica gel flash chromatography. The solvent system was CHCl$_3$/CH$_3$OH (9:1, 300 ml) followed by CHCl$_3$/CH$_3$OH/H$_2$O (65:25:3, 800 ml) Chromatography fractions containing product were pooled, concentrated by rotoevaporated and vacuum dried; the yield after chromatography was 0.96 g of white solid (88.8% yield). TLC in CHCl$_3$:CH$_3$OH:NH$_3$.H$_2$O (65:25:4) showed a pure product (Rf=0.44). FTIR: (thin film, cm$^{-1}$) 3384.65, 2923.00, 2852.32, 1742.15, 1715.33, 1690.96, 1553.86, 1517.93, 1464.04, 1365.55, 1244.64, 1221.96, 1171.99, 1108.70, 1071.16. $^1$H NMR (500 MHz, CDCl$_3$, δ ppm): 5.20 (1H, br, m), 4.36 (1H, d, J=10.5 Hz), 4.13 (1H, br, m), 3.93 (2H, br, m), 3.86 (2H, br, m), 3.33 and 3.20 (2H, br, m), 2.25 (6H, m), 1.55 (6H, m), 1.40 (9H, s), 1.25 (36H, m), 0.85 (3H, t, J=6.75 Hz). FAB-MS [M+Na$^+$] calcd for $C_{38}H_{71}NO_{12}P$ 789.0, found 788.5.

N-tert-Butyloxycarbonyl-)-allylester-1-myristoyl-2-(13-carboxytridecanoyl)-sn-3-phosphatidylserine (1d, $PS^{2\omega\text{-}COOH/P}$)

PC-COOH (7.0 g, 9.90 mmol) was dissolved in anhydrous chloroform (200 ml) using a 500 ml r.b. flask. Serine allyl ester (7.2 g, 49.50 mmol) was added to the reaction mixture followed by 33.4 ml of buffer (composed of 100 mM NaOAc, 50 mM CaCl$_2$ at pH 6.5). PLD (500 µl, 1.0 unit/µl in NaOAc buffer) was added and the reaction was stirred at 30° C. under N$_2$ for 8 hours. The chemical intermediate, a carboxyl PS analog from the PLD reaction of PC-COOH, was concentrated via rotoevaporation and not purified prior to the protecting the serine amine with Boc. The primary serine amine was protected with Boc as described above in the preparation of $PE^{2\omega\text{-}COOH/P}$. After acidification of the protection reaction mixture using KHSO$_4$ (160 ml, 1.0 M), the product was extracted using diethyl ether (4×100 ml). The diethyl ether extracts were pooled and the solvent rotoevaporated to obtain a yellow oil which was purified by silica gel flash chromatography using CH$_2$Cl$_2$/CH$_3$OH/H$_2$O (65:25:4) as the mobile phase. The amount of final product (white solid) obtained after column chromatography resulted in an 87% overall yield (7.32 g) TLC in CH$_2$Cl$_2$/CH$_3$OH (1:1) showed a pure product (Rf= 0.81). FTIR: (thin film, cm$^{-1}$) 3364.26, 2925.48, 2855.87, 1741.78, 1713.99, 1510.08, 1461.08, 1372.02, 1185.02, 1080.51. $^1$H NMR (300 MHz, CDCl$_3$, δ ppm): 5.90 (1H, m), 5.34–5.20 (4H, m), 4.62–4.00 (8H, m), 2.27 (6H, m), 1.57 (6H, m), 1.41 (9H, s), 1.25 (36H, br s), 0.87 (3H, tr, J=6.65 Hz). MALDI-MS [M–H]$^-$ calcd for $C_{42}H_{75}NO_{14}P$ 848.1, found 848.0.

$^{ester}$IAM.PG$^{C10/C3}$ (7)

$PG^{2\omega\text{-}COOH/P}$ (1a) (1.0 g, $^-$1.35 mmol) was suspended in anhydrous CHCl$_3$ (50 ml) using a r.b flask (100 ml) and CDI (0.380 g, 2.35 mmol) was added. The 1a ligand is not very soluble in CHCl$_3$, but, the CDI-activated $PG^{2\omega\text{-}COOH/P}$ ligand is very soluble. After overnight stirring at r.t., both TLC CH$_2$Cl$_2$/CH$_3$OH/H$_2$O (65:25:4) and IR spectroscopy indicated that CDI was completely consumed but only ~60% of the starting material was activated. Vacuum-dried SPA (RN39-94) (10.59 g) was added and the suspension was mixed using an orbital shaker (150 rpm, 24 hours). The $^{ester}$IAM.PG$^P$ silica was then filtered through an F glass-sintered funnel, washed with chloroform (2×20 ml), methanol (3×20 ml) and acetone (10 ml) followed by drying in a vacuum oven at 40° C. overnight. The coupling was repeated using reaction conditions corresponding to 0.25 equivalents of the $PG^{2\omega\text{-}COOH/P}$ ligand. C10 and C3 end-cappings were performed as described previously to obtain $^{ester}$IAM.PG$^{P/C10/C3}$. Deprotection of the isopropylidene protecting group on the $^{ester}$IAM.PG$^{P/C10/C3}$ surface was needed to generate an immobilized artificial membrane containing PG. Briefly, $^{ester}$IAM.PG$^{P/C10/C3}$ (~10.9 g) was suspended anhydrous CH$_2$Cl$_2$ (24 ml). Then anhydrous TEA (8 ml) was added to the suspension. After 2 h of shaking the silica was filtered, washed with CH$_2$Cl$_2$ (2×20 ml), CH$_3$OH (3×20 ml), and acetone (20 ml), followed by vacuum drying (40° C. overnight). The deprotection step was repeated with 50% TFA/50% CH$_2$Cl$_2$ (V/V, 24 ml) for 4.0 hours. Then the silica was immersed in 50% 1 M Na$_2$CO$_3$/50% CH$_3$OH (80 ml, 6 min) under constant stirring, followed by washing with water (600 ml), CH$_3$OH (2×40 ml) and acetone (2×40 ml). The surface was finally vacuum-dried at 40° C. overnight. FTIR microscopy of surface (7) indicated that the IPG group was quantitatively removed because the characteristic IPG peak at 1370.0 cm$^{-1}$ disappeared completely after the deprotection. The bonded ligand density[Ong, 1994 #14] (1a) on $^{ester}$IAM.PG$^P$ was 134.67 µmol/g-silica based on elemental analysis of carbon content before (C, 2.13%) and after (C, 7.46%) ligand 1a bonding to silica surfaces.

$^{ester}$IAM.PA$^{C10/C3}$ (8)

The bonding procedures for immobilizing PA$^{2\omega\text{-}COOH/P}$ (1b), C10 and C3 endcappings to prepare $^{ester}$IAM.PA$^{P/C10/C3}$ were the same as those used to prepare the $^{ester}$IAM.PG$^{P/C10/C3}$. Deprotection of p-nitrophenylethyl (NPE) group on the $^{ester}$IAM.PA$^{P/C10/C3}$ surface was performed as described. Briefly, $^{ester}$IAM.PA$^{P/C10/C3}$ (~15.0 g) was suspended in anhydrous CH$_2$Cl$_2$ (50 ml), then anhydrous DBU (20 ml) was added. After 2 h of shaking, the silica was filtered, washed with saline (1.0 M NaCl, 500 ml), H$_2$O (500 ml), and acetone (50 ml), followed by vacuum drying (40° C., overnight). Based on the integrated IR band of NPE between 1333–1358 cm$^{-1}$ before and after deprotection, this first deprotection step resulted in ~70% removal of p-nitrophenylethyl group. A second deprotection using benzene resulted in ~81%. After deprotection, the silica was filtered, washed with CHCl$_3$ (200 ml), CH$_3$OH (100 ml), saline (1.0 M NaCl, 500 ml), H$_2$O (500 ml) and acetone (100 ml) followed by vacuum drying (40° C. overnight). The bonded ligand density (1b) on $^{ester}$IAM.PA$^P$ was 96.50 μmol/g-silica based on elemental analysis of carbon contents before (C, 2.13%) and after (C, 6.34%) ligand 1b bonding to silica surfaces.

$^{ester}$IAM.PE$^{C10/C3}$ (9)

The bonding procedures for immobilizing PE$^{2\omega\text{-}COOH/P}$ (1b), C10 and C3 endcappings to prepare $^{ester}$IAM.PE$^{P/C10/C3}$ were the same as those used to prepare the $^{ester}$IAM.PG$^{P/C10/C3}$. Boc Deprotection from the $^{ester}$IAM.PE$^{P/C10/C3}$ surface was performed as described. Briefly, $^{ester}$IAM.PE$^{P/C10/C3}$ (~8.9 g) was suspended in anhydrous CH$_2$Cl$_2$ (20 ml). Then anhydrous TFA (20 ml) was added to the suspension. After 2 h of shaking, the silica was filtered, washed with CH$_2$Cl$_2$ (2×20 ml), CH$_3$OH (3×20 ml), and acetone (20 ml), followed by vacuum drying (40° C., overnight). The first deprotection was ~80% complete and a second deprotection step in 50% TFA/50% CH$_2$Cl$_2$ for 4.0 hours resulted in complete deprotection; the Boc IR band 1369.0 cm$^{-1}$ completely disappeared. The bonded ligand density (1c) on $^{ester}$IAM.PE$^P$ was 109.33 μmol/g-silica based on elemental analysis of carbon contents before (C, 2.13%) and after (C, 6.64%) ligand 1c bonding to silica surfaces.

$^{ester}$IAM.PS$^{C10/C3}$ (10)

The bonding procedures for preparing $^{ester}$IAM.PS$^{P/C3/C3}$ were the same as those used to prepare the $^{ester}$IAM.PG$^{P/C10/C3}$ except that double C3 endcapping was used. Deprotection of surface allyl ester group on $^{ester}$IAM.PS$^{P/C3/C3}$ was based on the solution deprotection conditions. Briefly, $^{ester}$IAM.PS$^{P/C3/C3}$ (22.44 g) was suspended in anhydrous CH$_2$Cl$_2$ (50 ml), nitrogen purged (5 min), sonicated (10 sec) and nitrogen purged (1 min) before adding the deprotection reagents. PdCl$_2$(PPh$_3$)$_3$ (96.07 mg, 0.14 mmol), acetic acid (600.4 μl, d=1.049, 10.50 mmol) and Bu$_3$SnH (4.53 ml, d=1.082, 16.84 mmol) were sequentially added to $^{ester}$IAM.PS$^{P/C3/C3}$ suspension. After 2 h of shaking, Bu$_3$SnH (1.0 ml, 3.72 mmol) was added and the suspensions were shaken for additional 30 minutes. The surface was filtered, washed with CH$_2$Cl$_2$ (50 ml), CH$_3$OH (5×50 ml), hexane (30 ml), ethyl acetate (30 ml) and acetone (40 ml), followed by vacuum drying (40° C., overnight). The deprotection procedure of the allyl ester was repeated prior to Boc deprotection. For Boc deprotection, the conditions described above to prepare the $^{ester}$IAM.PE$^{C10/C3}$ surface were used except that the deprotection reaction was performed once. Based on FTIR microscopy, quantitative deprotection occurred. The bonded ligand density on $^{ester}$IAM.PS$^P$ was 104.86 μmol/g-silica based on elemental analysis of carbon contents before (C, 2.13%) and after (C, 6.99%) ligand 1d bonding to silica surfaces

IAM.SM$^{C10/C3}$ (11)

The bonding procedures for immobilizing SM$^{\omega\text{-}COOH/P}$ (2), C10 and C3 endcappings to prepare IAM.SM$^{P/C10/C3}$ were the same as those used to prepare the $^{ester}$IAM.PG$^{P/C10/C3}$ except the ligand coupling to silica propylamine was performed only once. Deprotection of TBDPS protecting group on the SM headgroup was done as described. Briefly, IAM.SM$^{P/C10/C3}$ (~2.1 g) was suspended in THF (20 ml) before TBAF (20 ml, 1.0 M solution in THF) was added to the suspension. After 2 h of shaking, the silica was filtered, washed with THF (2×20 ml), CHCl$_3$ (3×20 ml), CH$_3$OH (3×20 ml), and acetone (20 ml), followed by vacuum drying (40° C., overnight). FTIR microscopy indicated that deprotected was quantitative; because the TBDPS IR peak at 3074.23 cm$^{-1}$ and 3056.10 cm$^{-1}$ completely disappeared. The bonded ligand density (2) on IAM.SM$^P$ was 90.53 μmol/g-silica based on elemental analysis of carbon content before (C, 2.04%) and after (C, 7.35%) ligand 2 bonding to silica surfaces.

Synthesis and Immobilization of Ceramide Analogs on the Silica Particles

The skin is the largest organ of the human body, a primary area contacted with the environment, and a route by which many chemical substances enter the body. Research has demonstrated that drug delivery through the skin is feasible for many simple potent drug molecules (less than 1000 Da) via transdermal drug delivery systems. Seven drugs marketed in United States including clonidine, estradiol, fentanyl, nicotine, nitroglycerin, scopolamine, and testosterone are delivered by transdermal systems. Through transdermal drug delivery systems, steady-state plasma concentrations of a drug can be achieved without the high peak levels associated with oral therapy. The avoidance of high peak levels may help minimize the side effects of certain drugs. Meanwhile denial exposure to toxic substances represents a major occupational hazard; successful anticipation of potential risk could significantly reduce the incidence of chronic health and environmental problems. The interest in the skin has encouraged research in the field and has led to a better understanding of skin biological structure. The studies have showed that the major permeability barrier of the human skin is provided by its outer layer—the stratum corneum (SC). The stratum corneum consists of dead cells surrounded by an extracellular matrix containing lipid lamellae. The major lipid components of this extracellular matrix is ceramides which comprise 50% of the total lipid and consist six structurally heterogeneous ceramides. Among them, ceramide 2 comprises 40% of the total ceramides. Ceramide consists of mainly 24- through 28-carbon fatty acids amide-linked to sphingosine and dihydrosphingosine bases.

Studies of model systems capable of predicting plasma levels following topical administration are continuously being pursued. These investigations aim at facilitating the rational selection of transdermal drug candidate which can penetrate skin barrier or predicting the potential risk of dermal exposure to toxic chemicals. By immobilizing skin lipids such as ceramide 2 on a chromatographic support there is provided a new model system to evaluate chemical skin interaction. The chemical skin interactions can then be chromatographically measured via HPLC. This system would be much better than octanol/water partition system and more feasible than laborable and controlled measurement of skin permeability in vivo. The ceramide ligand (N-[13-carboxyltridecanoyl]-D-erythro sphingosine 2) used to prepare ceramide silica surface contains basic ceramide 2 functional moiety, and a free ω-carboxyl group. The free ω-carboxyl group functions as a tag to the silica propyl amine particles through 1,1'-carbonyldiimidazole (CDI) activation. Anhydrides are used to endcap excess amine groups on the silica propyl amine particles. See Scheme 5.

SCHEME 5
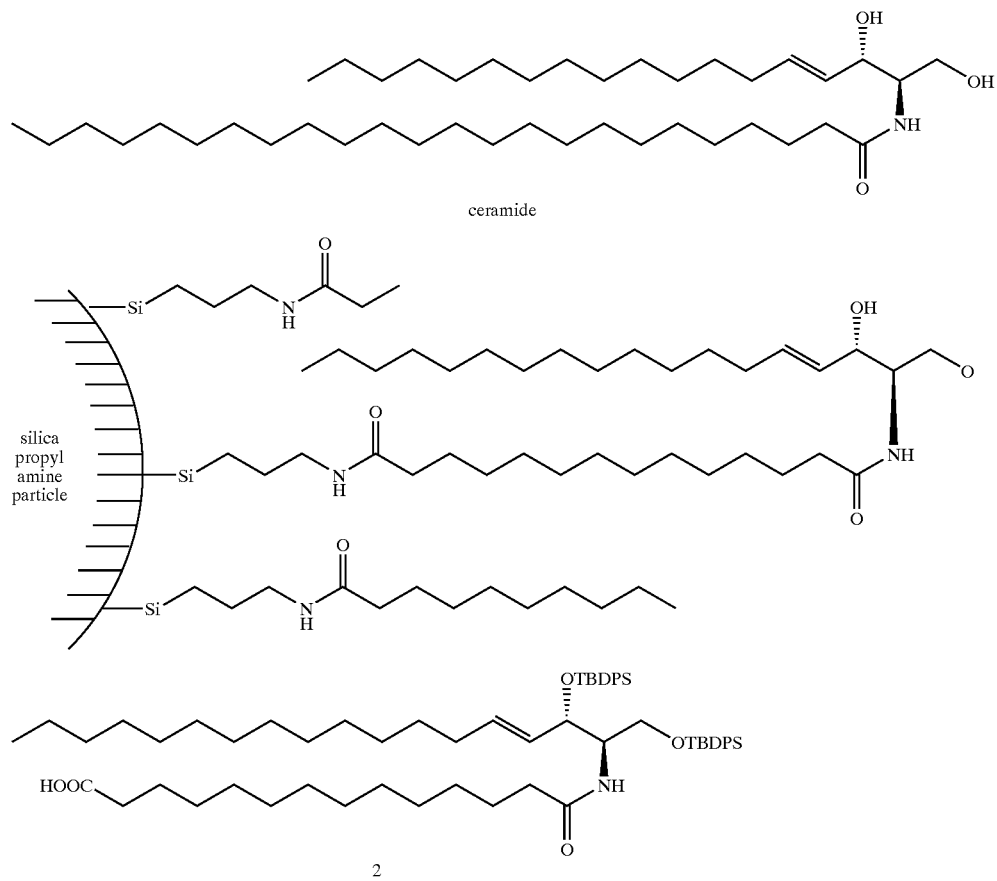
SCHEME 6
Synthetic route of silica-immobilized ceramide stationary phase.
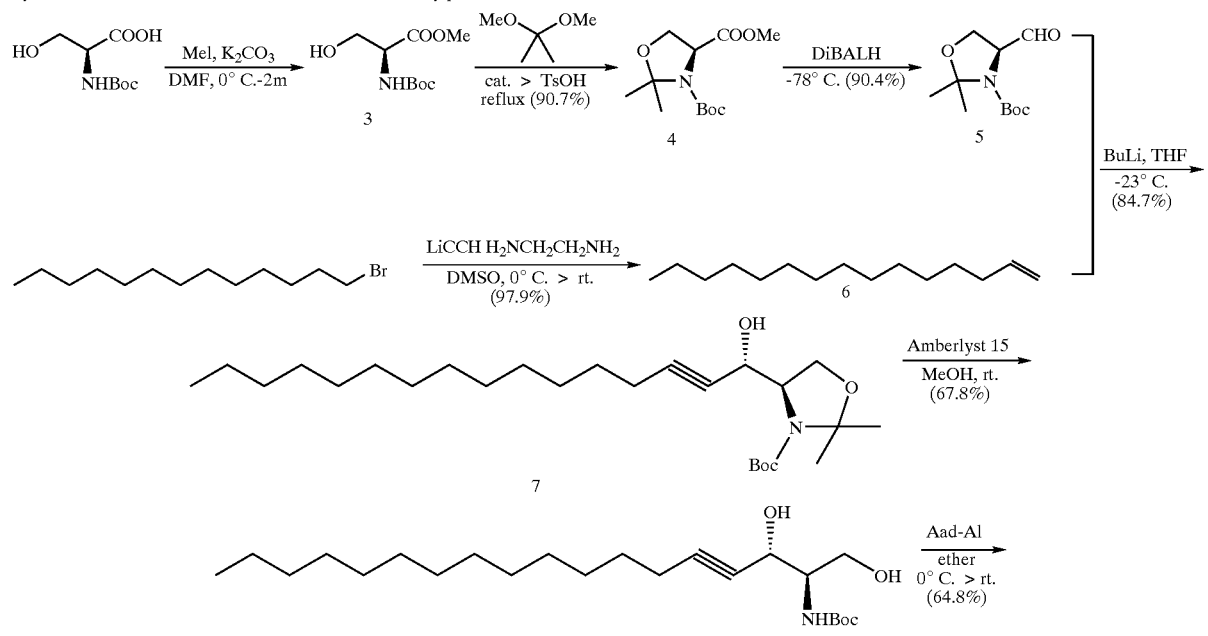

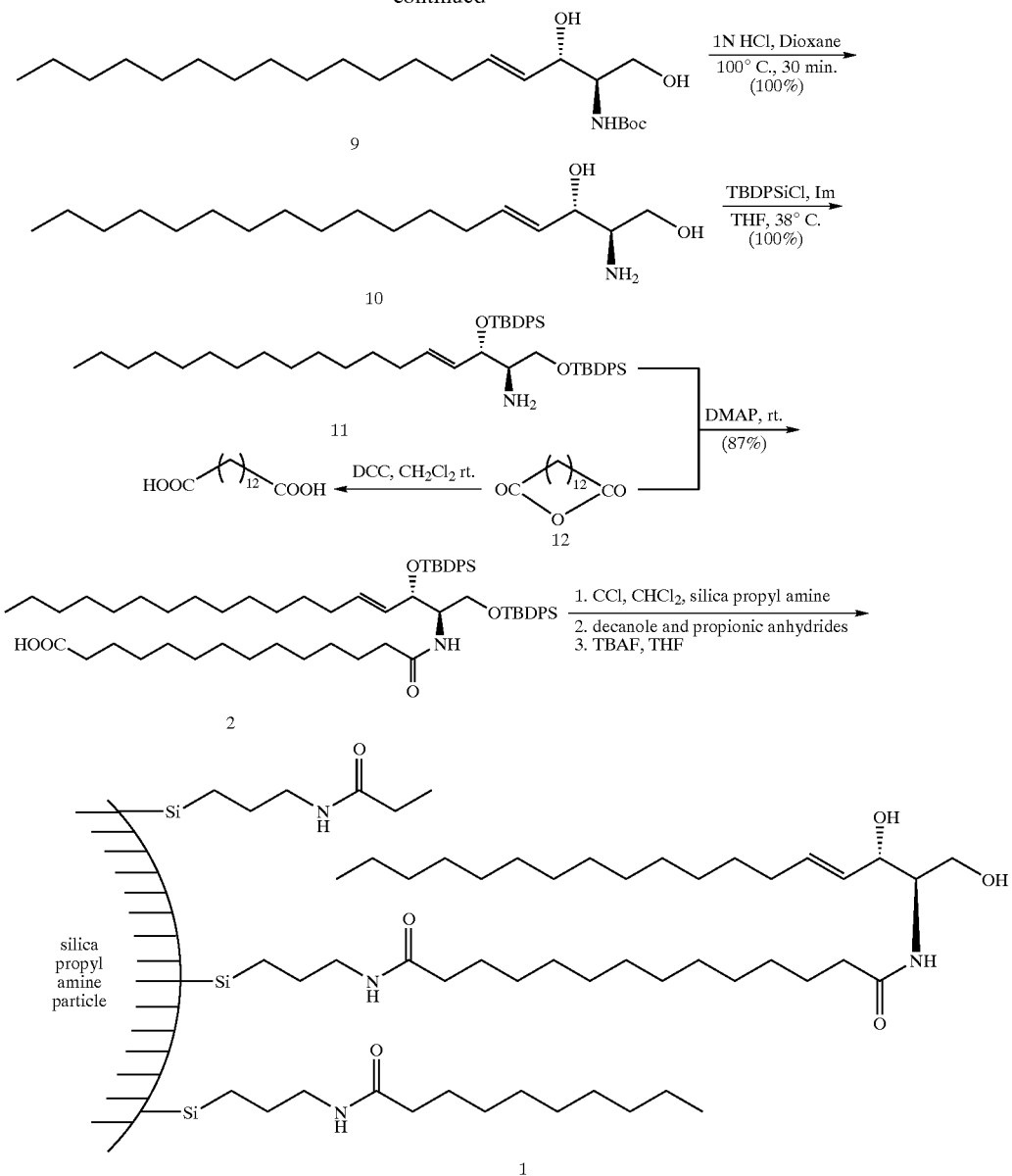

DIBALH: Disobutylaluminum hydride
TBDPSCl: tert-Butyldiphenylallyl chloride
DCC: Dicyclohexylcarbodimide
DMAP: 4-Dimethylaminopyridine
CDI: Carbonydimidazole
TBAF: Tetrabutylammonium Flouride A representative synthesis of ceramide stationary surfaces is outlined in Scheme 6. The treatment of N-Boc-L-serine with methyl iodide gave N-Boc-L-serine methyl ester 3 which was reacted with 2,2-dimethoxypropane under the catalysis of p-toluenesulfonic acid monohydrate to produce the acetal protected compound 4, which was reduced to the aldehyde 5 under mild reduction (using diisobutylaluminum hydride (DIBALH) as reagent and running the reaction at −78° C.). Meanwhile, 1-pentadecyne 6 was synthesized from 1-bromotridecane and lithium acetylide ethylenediamine complex in dimethyl sulfoxide (DMSO) solution. Then oxazolidine aldehyde 5 was treated with lithium acetylide (from 1-pentadecyne 6 and n-butyl lithium) at −23° C. to produce the basic structure of sphingosine 7 in 84% yield after flash chromatography. High erythroselectivity (with diastereoselectivity (ds) ~89%) was observed in this reaction. Treatment of compound 7 with mild acid Amberlyst 15 in methanol at room temperature resulted in selective cleavage of the acetal protecting group, leading to the 1,3-diol 8 which was converted to N-Boc-sphingosine 9 by selective reduction of the triple carbon bond with Red-A1 in ether. This reduction condition specifically converted the triple bond to the trans double bond. Cleavage of the carbamate moiety with 1.0 N HCl in dioxane at 100° C. resulted in D-erythro-sphingosine 10 which was reacted with tert-butyldiphenylsily chloride (TBDPSCl) in order to protect the two hydroxyl groups. The TBDPS group is considerably more stable (about 100 times) than the tert-butyldimethylsilyl (TBDMS) group toward acidic hydrolysis and therefore is appropriate for the immobilization reaction. Subsequent reaction of TBDPS-protected sphingosine 11 with dodecanedicarboxylic acid anhydride 12 (a cyclic anhydride, synthesized from diacid and dicylohexylcarbodiimide (DCC)) in chloroform afforded N-[13-carboxyltridecanoyl]-D-erythro-sphingosine 2 under catalysis of 4-dimethylaminopyridine (DMAP) in 87% yield after flash chromatography. The ω-carboxyl group of ceramide analog 2 was activated with CDI in chloroform. Following the activation, the ceramide-imidazolides were bonded to silica propylamine (SPA) particles with 24 hours shaking. After workup, ceramide-based silica stationary phase was obtained and subjected to C10 and C3 endcapping of the residual amines on the silica particle surface. The TBDPS protecting groups were removed with tetrabutylammonium fluoride(TBAF) in THF. The reactions were monitored by a Nicolet Magna 550 FT-IR spectrometer equipped with a Spectratech IR-Plan I microscope. After deprotection, a monolayer of ceramide lipid membrane is generated bearing identical interfacial groups to endogenous ceramide lipid. The bonding density was calculated from elemental analysis. Finally these silica particles were packed into the stainless-steel columns and used for high performance liquid chromatography. Our preliminary data clearly showed that ceramide based stationary phases are suitable for the prediction of skin permeability constants of diverse chemicals. Solute capacity factors (k') measured on the columns correlated well with skin permeability coefficients (kp) or the percentage of percutaneous absorption (% Abs) measured through the excised human skin or the human subjects.

Correlation of Drug Binding Affinities with Oral Absorption

Table 6 shows eight compounds eliciting low oral absorption that were used as a training set to calculate a $^{low}MAF^\mu$ representative of low drug absorption. The small average $D^2$ value, i.e., 3.5±1.24 relative to $^{low}MAF^\mu$ (last column in Table 6) indicates that the group of compounds in the training set are statistically well defined. $D^2$ values based on $^{low}MAF^\mu$ for the 13 compounds exhibiting complete oral absorption are very high (Table 7). The large average $D^2$ value, i.e., 96.26±96.01 (last column in Table 7) indicates that compounds which are highly absorbed have statistically different membrane binding properties compared to compounds that exhibit low oral absorption.

TABLE 6

Training Set Representing Low Oral Absorption

| Compound | Oral Absorption (%) | $D^{2**}$ |
|---|---|---|
| nalbuphine | 16 | 2.10 |
| ketamine | 20 | 3.71 |
| scopolamine | 27 | 2.13 |
| norfloxacin | 30 | 4.96 |
| sulpiride | 36 | 4.95 |
| acebutolol | 37 | 2.87 |
| ranitidie | 50 | 4.67 |
| etoposide | 50 | 2.58 |
|  | Average = 3.5 ± 1.24 | |

*These eight compounds were used to determine the $^{low}MAF^\mu$ vector.
**$D^2$ values are calculated relative to the $^{low}MAF^\mu$ vector.

Since the test compounds in Table 7 exhibited distinct $D^2$ values compared to the $^{low}MAF^\mu$ vector, the compounds listed in Table 7 were used as a potential training set to generate a $^{high}MAF^\mu$ vector.

TABLE 7

Calculation of $D^2$ Relative to $^{low}MAF^\mu$ for Compounds That are Completely Absorbed

| Compound | Oral Absorption (%) | $D^2$ |
|---|---|---|
| clonidine | 95 | 22.4 |
| clofibrate | 95 | 234 |
| alprenolol | 96 | 27.8 |
| metronidazole | 98 | 81.8 |
| indomethacin | 98 | 65.3 |
| clonazepam | 98 | 151 |
| desmethyldiazepam | 99 | 328 |
| phenytoin | 100 | 7.17 |
| phenobarbital | 100 | 17.3 |
| diazepam | 100 | 138 |
| corticosterone | 100 | 17.2 |
| chlordiazepoxide | 100 | 103 |
| caffeine | 100 | 58.4 |
|  | Average = 96.26 ± 96.01 | |

Table 8 shows $D^2$ values relative to $^{high}MAF^\mu$ for each compound in the high drug absorption training set. $D^2$ values based on $^{high}MAF^\mu$ for the 8 compounds exhibiting low oral absorption are high (Table 9).

TABLE 8

Training Set Representing High Oral Absorption

| Compound* | Oral Absorption (%) | $D^{2**}$ |
|---|---|---|
| chlordiazepoxide | 100 | 1.26 |
| diazepam | 100 | 1.67 |
| clofibrate | 95 | 1.85 |
| clonazepam | 98 | 1.89 |
| alprenolol | 96 | 2.48 |
| phenobarbital | 100 | 2.99 |
| corticosterone | 100 | 3.05 |
| phenytoin | 100 | 3.16 |
| chlonidine | 95 | 4.87 |
| desmethyldiazepam | 99 | 5.57 |
| indomethacin | 98 | 5.75 |
| caffeine | 100 | 6.22 |
| metronidazole | 98 | 7.15 |
|  | Average = 3.68 ± 1.97 | |

*These compounds were used to determine the $^{high}MAF^\mu$ vector.
**$D^2$ values are the calculated relative to the $^{high}MAF^\mu$ vector.

TABLE 9

Calculation of $D^2$ Relative to $^{high}MAF^\mu$ for Compounds That Have Low Oral Absorption

| Compound* | Oral Absorption (%) | $D^{2**}$ |
|---|---|---|
| nalbuphine | 16 | 2.20 |
| ketamine | 20 | 7.87 |
| scopolamine | 27 | 2.53 |
| norfloxacin | 30 | 39.4 |
| sulpiride | 36 | 3.94 |
| acebutolol | 37 | 2.05 |
| ranitidine | 50 | 42.09 |
| etoposide | 50 | 3.36 |
|  | Average = 12.9 ± 17.3 | |

Data Acquisition Using Liquid Chromatograph/
Mass Spectrometer (LCMS)—General
Experimental Protocol Mass spectrometers (MS) can be used as detectors for identification of compound eluting from a liquid chromatograph (LC) instrument. The only requirement for detection is that the compound can be ionized without composition. Thus, one preferred method for determining membrane binding constants is to use an MS as a detector for compounds eluting from LC columns. The general advantages of using MS detection are (1) compounds without chromophores can easily be detected, (2) multiple compounds can be uniquely identified from a single injection, and (3) small amounts of compound can be used for determination of binding constants chromatographically measured on immobilized artificial membranes (IAMs) or other solid phase chromatographic substrates. These three advantages allow simultaneous injection of very small amounts of hundreds of compounds with detection of essentially all compounds eluting from the column. Such procedure allows for direct comparison of binding affinities of a large number of test compounds with multiple compounds comprising one or more training sets, thereby eliminating inherent data variability deriving from column-to-column variability and variability in other experimental parameters. An example of data acquisition using LC with MS detection is given below.

Test Mixture

A mixture containing 0.100 μmoles of 155 compounds was prepared. At least a portion of the compounds are compounds of known clinical significance; they serve as internal standards against which the binding affinities of the test compounds are measured. The mixture was dissolved in 6.0 mL 15% acetonitrile and 85% 30 mM ammonium acetate, pH—7.4. 20 μL of this test mixture was loaded onto a 3×0.46 cm IAM column. This corresponds to loading ~16 μg of the test mixture and loading ~320 pmoles of each compound onto the column.

LC Conditions

A 3×0.46 cm IAM column was used. The mobile phase was 15% acetonitrile and 85% 30 mM ammonium acetate, pH—7.4. The flow rate was 1.0 mL per minute and no flow splitter was used. The run time was 2 hours followed by a 10 minute 100% acetonitrile wash.

MS Conditions

A Bruker Esquire-LC was used. Each run was done twice. In the first run, the auto MS/MS was not used. In the second run, the auto MS/MS was used. The auto MS/MS allows for the identification of compounds which have the same molecular weight.

Typical MS instrument have the capacity to use flow rates of 2 mL/min and at least one instrument has a mechanism for washing salts from the inlet of the ion source. Typically, mobile phases cannot have salts because evaporation of the mobile phase in the ion source results in excess buildup of salts that restrict flow of ions into the ion source. Finnigan recently developed an LC/MS instrument in which salts are washed away during the chromatography process. Affinity data are collected and stored electronically in a storage device as output from the MS detector and thereafter processed, typically using a computer data accessible communication with the data storage device, and programmed with a vector analysis algorithm, to provide a user readable output in a preprogrammed format for facilitating comparison of the binding affinities of test compounds with those of control compounds or with mean vector quantities for one or more training sets.

What is claimed is:

1. A method of screening test compounds for probable biological activities comprising the steps of identifying two or more membrane mimetic surfaces each having a unique composition;

providing a set of control compounds, each control compound having a known biological activity and defining for each control compound an ordered set of numerical values related to its interaction with each respective membrane mimetic surface, whereby said ordered set of numerical values can be represented by the expression $\{C_1, C_2 \ldots C_n\}$ wherein n is the number of membrane surfaces;

defining an ordered set of numerical values $\{T_1, T_2 \ldots T_n\}$ for each test compound related to its interaction with each respective membrane mimetic surface; and comparing the set of numerical values for each test compound with the sets of respective values for said control compounds and identifying the biological activities of those control compounds having ordered sets of numerical values best matching the respective numerical values in the ordered set of values for each test compound, wherein the best matching control compounds are those for which the angle θ in the formula cosine $\theta = (T_1 C_1 + T_2 C_2 + \ldots T_n C_n)/(T_1^2 + T_2^2 + \ldots T_n^2)^{1/2} (C_1^2 + C_2^2 \ldots C_n^2)^{1/2}$ is less than about 20°.

2. The method of claim 1 wherein at least a portion of the numerical values are calculated.

3. The method of claim 1 wherein numerical values relating to the interaction of the compounds with each membrane mimetic surface are determined in a chromatographic system using a mobile phase and a stationary phase comprising said membrane mimetic surface.

4. The method of claim 3 wherein each value in the ordered set of numerical values for each respective compound corresponds to the retention time of the compounds in the chromatographic system using a predetermined stationary phase.

5. The method of claim 3 wherein each value in the ordered set of numerical values for each respective compound corresponds to the peak width of the compounds in the chromatographic system using a predetermined stationary phase.

6. The method of claim 3 wherein each membrane mimetic surface is an immobilized artificial membrane.

7. The method of claim 1 wherein at least one of the membrane mimetic surfaces comprises a head group of a phospholipid compound that occurs naturally in biological membranes.

8. The method of claim 1 wherein the membrane mimetic surfaces are selected from liposomes, Langmuir-Blodgett films, and immobilized artificial membranes.

9. The method of claim 1 wherein the numerical values for T and C for each membrane surface are each normalized against a common reference standard for said membrane surface.

10. The method of claim 1 wherein the angle θ is less than about 15°.

11. The method of claim 1 wherein the angle θ is less than about 10°.

12. The method of claim 1 wherein at least one of the membrane mimetic surfaces comprises a mixture of lipid compounds.

13. A system for screening test compounds for probable biological activities in accordance with the method of claim 1, said apparatus comprising two or more membrane mimetic surfaces, each having a unique composition, means for quantifying the interaction of the test compounds and control compounds with each of the membrane mimetic surfaces and means for assigning a numerical value characteristic of said quantified interaction of the compounds for each respective membrane mimetic surface; and a programmable computer for comparing the numerical values for the test compounds for each of the membrane mimetic surfaces with the numerical values for the control compounds for each of the membrane mimetic surfaces.

14. The test system of claim 13 further including a printer, a display or other means for reporting the control compounds having numerical values best matching those of the test compounds.

15. The test system of claim 13 further comprising a database containing numerical values characteristic of the interaction of selected control compounds for each membrane mimetic surface, at least a portion of said selected control compounds having a predefined biological activity.

16. The test system of claim 13 wherein the quantifying means is a chromatographic system and the membrane mimetic surfaces are stationary phases for said system.

17. A method of screening test compounds for biological activities comprising selecting two or more membrane mimetic surfaces each having a unique composition, selecting at least one training set composition comprising one or more control compounds having a common biological activity, combining the test compounds with the training set composition to provide a test mixture;

contacting at least a portion of said test mixture with each of the membrane mimetic surfaces to define an ordered set of numerical values $\{T_1, T_2 \ldots T_n\}$ characteristic of the interaction of each test compound with the respective membrane mimetic surfaces and an ordered set of mean numerical values $\{Cm_1, Cm_2 \ldots Cm_n\}$ characteristic of the interaction of the training set compounds; and comparing the numerical values to identify test compounds having numerical values that best match the mean numerical values for the training set compounds, wherein the best matching test compounds are those for which the angle $\theta$ in the formula cosine $\theta = (T_1 Cm_1 + T_2 Cm_2 + \ldots T_n Cm_n)/(T_1^2 + T_2^2 + \ldots T_n^2)^{1/2}(Cm_1^2 + Cm_2^2 \ldots Cm_n^2)^{1/2}$ is less than about 20°.

18. The method of claim 17 wherein the step of contacting the test mixture with the membrane mimetic surfaces is carried out in a chromatographic system wherein each membrane mimetic surface is a stationary phase in said system.

19. The method of claim 18 wherein the chromatographic system is a liquid chromatographic system utilizing a mass spectrometric detector.

20. The method of claim 18 wherein the step of comparing the numerical values includes the step of calculating a mean vector for the control compounds in each training set.

21. A method of screening test compounds for probable biological activities comprising the steps of identifying two or more membrane mimetic surfaces each having a unique composition;

providing a set of control compounds, each control compound having a common biological activity and defining for each control compound an ordered set of numerical values related to its interaction with each respective membrane mimetic surface, whereby said ordered set of numerical values can be represented by the expression $\{C_1, C_2 \ldots C_n\}$ wherein n is the number of membrane surfaces;

calculating an ordered set of mean values for said control compounds represented by the set $\{Cm_1, Cm_2 \ldots Cm_n\}$;

defining an ordered set of numerical values $\{T_1, T_2 \ldots T_n\}$ for each test compound related to its interaction with each respective membrane mimetic surface; and identifying those test compounds having ordered sets of numerical values best matching the ordered set of mean values for the control compounds wherein the best matching test compounds are those for which the angle $\theta$ in the formula cosine $\theta = (T_1 C_1 + T_2 C_2 + \ldots T_n C_n)/(T_1^2 + T_2^2 + \ldots T_n^2)^{1/2}(C_1^2 + C_2^2 \ldots C_n^2)^{1/2}$ is less than about 20°.

22. The method of claim 21 wherein at least a portion of the numerical values are calculated.

23. The method of claim 21 wherein numerical values relating to the interaction of the compounds with each membrane mimetic surface are determined in a chromatographic system using a mobile phase and a stationary phase comprising said membrane mimetic surface.

24. The method of claim 21 wherein at least one of the membrane mimetic surfaces comprises a head group of a phospholipid compound that occurs naturally in biological membranes.

25. The method of claim 24 wherein each value in the ordered set of numerical values for each respective compound corresponds to the retention time of the compounds in the chromatographic system using a predetermined stationary phase.

26. The method of claim 24 wherein each value in the ordered set of numerical values for each respective compound corresponds to the peak width of the compounds in the chromatographic system using a predetermined stationary phase.

27. The method of claim 24 wherein each membrane mimetic surface is an immobilized artificial membrane.

28. The method of claim 21 wherein the membrane mimetic surfaces are selected from liposomes, Langmuir-Blodgett films, and immobilized artificial membranes.

29. The method of claim 21 wherein the numerical values for T and C for each membrane surface are each normalized against a common reference standard for said membrane surface.

30. The method of claim 21 wherein at least one of the membrane mimetic surfaces comprises a mixture of lipid compounds.

* * * * *